United States Patent
Hayden et al.

(10) Patent No.: US 11,021,702 B2
(45) Date of Patent: Jun. 1, 2021

(54) METHOD OF PRODUCING A NORMALISED NUCLEIC ACID LIBRARY USING SOLID STATE CAPTURE MATERIAL

(71) Applicant: Agriculture Victoria Services Pty Ltd, Attwood (AU)

(72) Inventors: Matthew James Hayden, Templestowe (AU); Stephane Laurent Kong Kaw Wa, Bundoora (AU)

(73) Assignee: Agriculture Victoria Services PTY LTD, Bundoora (AU)

( * ) Notice: Subject to any disclaimer, the term of this patent is extended or adjusted under 35 U.S.C. 154(b) by 919 days.

(21) Appl. No.: 14/430,786

(22) PCT Filed: Sep. 20, 2013

(86) PCT No.: PCT/AU2013/001089
§ 371 (c)(1),
(2) Date: Mar. 24, 2015

(87) PCT Pub. No.: WO2014/047678
PCT Pub. Date: Apr. 3, 2014

(65) Prior Publication Data
US 2015/0252361 A1 Sep. 10, 2015

(30) Foreign Application Priority Data
Sep. 25, 2012 (AU) .................. 2012904173

(51) Int. Cl.
*C12Q 1/68* (2018.01)
*C12N 15/10* (2006.01)
*C12Q 1/6806* (2018.01)

(52) U.S. Cl.
CPC ..... *C12N 15/1068* (2013.01); *C12N 15/1093* (2013.01); *C12Q 1/6806* (2013.01)

(58) Field of Classification Search
None
See application file for complete search history.

(56) References Cited

U.S. PATENT DOCUMENTS 6,150,112 A * 11/2000 Weissman ............ C12Q 1/6858
435/6.12
6,287,825 B1 * 9/2001 Weissman .......... C12N 15/1096
435/6.13
(Continued)

FOREIGN PATENT DOCUMENTS

WO 2008121384 A1 10/2008

OTHER PUBLICATIONS

Hayden et al. (Nucleic Acids Research, 2001, 29(8):e43, p. 1-8) (Year: 2001).*

(Continued)

*Primary Examiner* — Stephanie K Mummert
(74) *Attorney, Agent, or Firm* — Larson & Anderson, LLC

(57) ABSTRACT

The present invention provides a method of preparing a nucleic acid library, which includes providing a one or more nucleic acid samples, and a one or more of samples of solid state capture material; contacting each nucleic acid sample with a sample of capture material to provide captured nucleic acid samples; and pooling the captured nucleic acid samples to provide the nucleic acid library. The method is particularly suitable for preparing nucleic acids for sequencing, especially next generation sequencing and related methods such as genotyping-by-sequencing.

11 Claims, 13 Drawing Sheets

Figure 1:
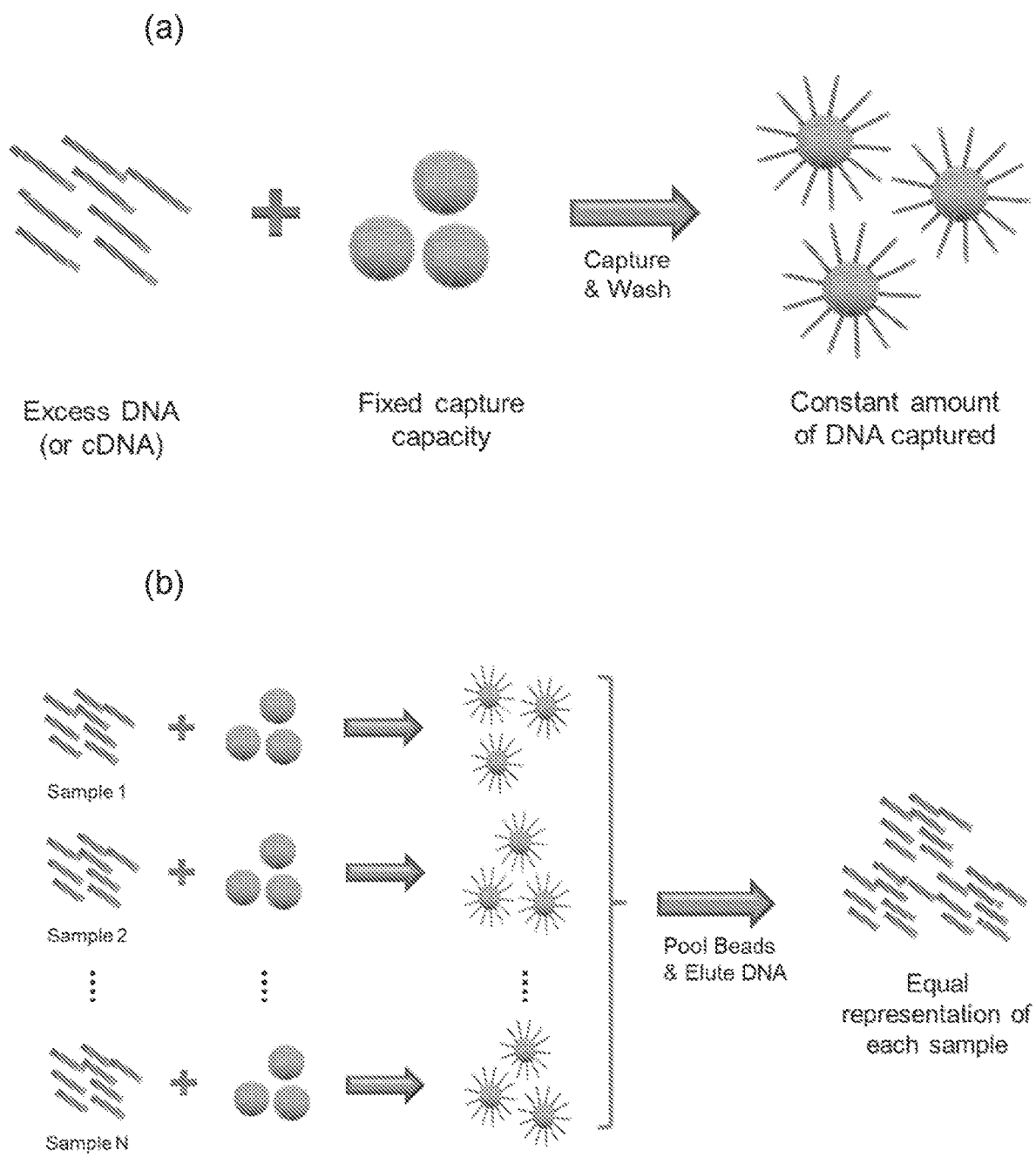

Specification includes a Sequence Listing.

(56) References Cited

U.S. PATENT DOCUMENTS

| | | | |
|---|---|---|---|
| 9,150,852 B2* | 10/2015 | Samuels | C12N 15/1075 |
| 2006/0269940 A1 | 11/2006 | Li et al. | |
| 2012/0015821 A1* | 1/2012 | Raymond | C12N 15/1093 |
| | | | 506/2 |
| 2013/0225418 A1* | 8/2013 | Watson | C12Q 1/6806 |
| | | | 506/2 |

OTHER PUBLICATIONS

Adey, A. et al., Rapid, low-input, low-bias construction of shotgun fragment libraries by high-density in vitro transposition, Genome Biology, 2010, R119, vol. 11.

Illumina: Nextera XT DNA Sample Preparation kit data sheet, Jun. 4 2012, [retrieved on Oct. 17, 2013] Retrieved from the Internet , <URL: http://res.illumina.com/documents/products/datasheets/datasheet_nextera_xt_dna_sample_prep.pdf.

Invitrogen: SequalPrep Normalization plate (96) Kit data sheet, May 5, 20058, [retrieved on Oct. 17, 2013]. Retrieved from the Internet <URL: http://tools.lifetechnologies.com/content/sfs/rnanuals/sequalprep_platekit_man.pdf.

Qiagen: SeqTarget Normalization Handook, Jan. 2010 [retrieved on Oct. 17, 2013]. Retrieved from the Internet <URL: http://www.qiagen.com/resources/download.aspx?id=40cebba0-138f-4250-af26-cbaf1918f9d2&lang=EN&vetr=1.

Wang, Z. et al., A Magnetic Bead-Integrated Chip for the Large Scale Manufacture of Normalized esiRNAs, PLoS one, 2012, pp. 1-7, e39419, vol. 7, Issue 6.

Berry, D. et al., Barcoded Primers Used in Multiples Amplicon Pyrosequencing Bias Amplification, Applied and Environmental Microbiology, 2011, pp. 7846-7849, vol. 77, No. 21.

* cited by examiner

```
mpxPE1supp Primer      A*ATGATACGGGCGACCACCGAGATCT
mpxPE1 Primer          A*ATGATACGGGCGACCACCGAGATCTACA CTCTTTCCCTACACGAC
mpxPE1 Primer          /5Biosg/A*ATGATACGGGCGACCACCGAGATCTACA CTCTTTCCCTACACGAC
gbsPE1 Primer                                    ACA CUCTTTCCCTACACGACGCT
Biotin-gbsPE1 Primer           /5Biosg/ACA CUCTTTCCCTACACGACGCT
mpxPE1ds.adp (+)                        /5Biosg/A*CUCTTTCCCTACACGACGCTCTTCCGATCTNNNNNN*T
mpxPE1ds.adp (-)                                  T*GAGAAAGGGATGTGCTGCGAGAAGGCTAGANNNNNN mpxPE2supp Primer      C*AAGCAGAAGACGGCATACGAGAT
mpxPE2 Primer          C*AAGCAGAAGACGGCATACGAGATNNNNNNNGTG ACTGGAGTTCAGACGTGT
gbsPE2 Primer                                    GTG ACTGGAGTTCAGACGTGTGCT
mpxPE2ds.adp (+)                        G*ACTGGAGTTCAGACGTGTGCTCTTCCGATCTNNNNNN*T
mpxPE2ds.adp (-)                        C*TCACCTCAAGTCTGCACACGAGAAGGCTAGANNNNNN /5Biosg/ACUCTTTCCCTACACGACGCTCTTCCGATCTNNNNNNTxxxxxxxxxANNNNNNAGATCGGAAGAGCGTCGTGTAGGGAAAGAGT
TGAGAAAGGGATGTGCTGCGAGAAGGCTAGANNNNNNAxxxxxxxxxTNNNNNNNTCTAGCCTTCTCGCAGCACATCCCTTTCTCA/5Biosg/
        mpxPE1                                                                    mpxPE1

/5Biosg/ACUCTTTCCCTACACGACGCTCTTCCGATCTNNNNNNTxxxxxxxxxANNNNNNAGATCGGAAGAGCACACGTCTGAACTCCAGTC
TGAGAAAGGGATGTGCTGCGAGAAGGCTAGANNNNNNAxxxxxxxxxTNNNNNNNTCTAGCCTTCTCGTGTGCAGACTTGAGGTCAG
        mpxPE2                                                                    mpxPE2

GACTGGAGTTCAGACGTGTGCTCTTCCGATCTNNNNNNTxxxxxxxxxANNNNNNAGATCGGAAGAACGGCACACGTCTGAACTCCAGTC
CTGACCYCAAGTCTGCACACGAGAAGGCTAGANNNNNNAxxxxxxxxxTNNNNNNTCTAGCCTTCTCGTGCAGACTTGAGGTCAG
        mpxPE2                                                                    mpxPE2
```

Figure 3a mpxPE1supp Primer    A*ATGATACGGGCGACCACCGAGATCT
mpxPE1 Primer        A*ATGATACGGCGACCACCGAGATCTACA CTCTTTCCCTACACGAC
mpxPE1 Primer        /5Biosg/A*ATGATACGGGCGACCACCGAGATCTACA CTCTTTCCCTACACGAC
gbsPE1 Primer                                       ACA CTCTTTCCCTACACGACGCT
Biotin-gbsPE1 Primer                           /5Biosg/ACA CTCTTTCCCTACACGACGCT
mpxPEy.adp(+)                                              /5Biosg/A*CTCTTTCCCTACACGACGCTCTTCCGATCTNNNNNN*T
mpxPEy.adp(-)                                                    C*TGACCTCAAGTCTGCACACGAGAAGGCTAGANNNNNNN
gbsPE2 Primer                                                     GTG ACTGGAGTTCAGACGTGTGCT
mpxPE2 Primer                                    C*AAGCAGAAGACGGCATACGAGATNNNNNNGTG ACTGGAGTTCAGACGTGT
mpxPE2supp Primer                                C*AAGCAGAAGACGGCATACGAGAT /5Biosg/ACUCTTTCCCTACACGACGCTCTTCCGATCTNNNNNTXXXXXXXXXXANNNNNNNAGATCGGAAGAGCACACGTCTGAACTCCAGTC
CTGACCTCAAGTCTGCACACGAGAAGGCTAGANNNNNNAXXXXXXXXXXTNNNNNNTCTAGCCAAGAGCCAGCACATCCCTTTCTCA/5Biosg/
mpxPEy                                                                                    mpxPEy

Figure 3b

Figure 4

TruSeq DNA Sample Prep Kit v2

Figure 8A:
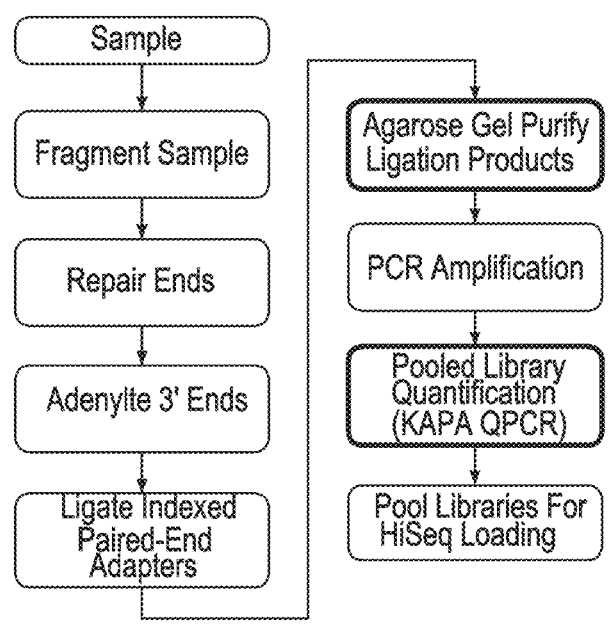

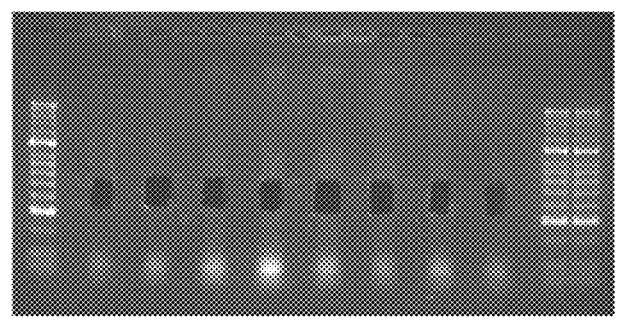
Gel excision + purification (~24 samples per day)
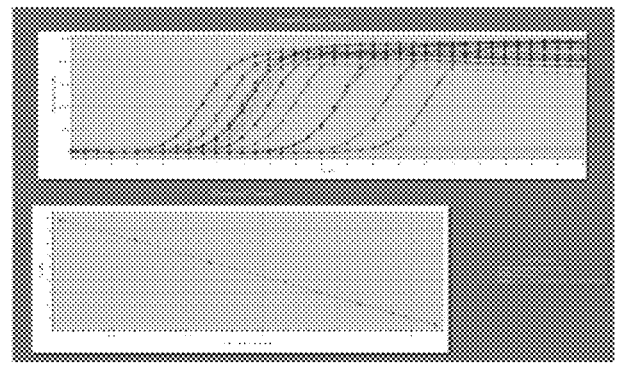
KAPA titrations (~50 libraries per machine per day)
Figure 8b

SEQUENCE LISTING

<160> NUMBER OF SEQ ID NOS: 24

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
aatgatacgg cgaccaccga gatct                                25

<210> SEQ ID NO 2
<211> LENGTH: 45
<212> TYPE: DNA
<213> ORGANISM: Artificial Sequence
<220> FEATURE:
<223> OTHER INFORMATION: Primer

<400> SEQUENCE: 2
aatgatacgg cgaccaccga gatctacact ctttccctac acgac          45

<210> SEQ ID NO 3
<211> LENGTH: 22
<212> TYPE: DNA
<213> ORGANISM: Artificial Sequence
<220> FEATURE:

<223> OTHER INFORMATION: Primer

<400> SEQUENCE: 3 acacucuuccc ctacacgacg ct                                   22

<210> SEQ ID NO 4
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (32)..(37)
<223> OTHER INFORMATION: n is a, c, g, t or u

<400> SEQUENCE: 4
acuctttccc tacacgacgc tcttccgatc tnnnnnnt                   38

<210> SEQ ID NO 5
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (32)..(37)
<223> OTHER INFORMATION: n is a, c, g, t or u

<400> SEQUENCE: 5
tgagaaaggg atgtgctgcg agaaggctag annnnnn                    37

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
caagcagaag acggcatacg agat                                  24

<210> SEQ ID NO 7
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (25)..(30)
<223> OTHER INFORMATION: n is a, c, g, t or u

<400> SEQUENCE: 7
caagcagaag acggcatacg agatnnnnnn gtgactggag ttcagacgtg t    51

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
gtgactggag ttcagacgtg tgct                                  24

```
<210> SEQ ID NO 9
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (33)..(38)
<223> OTHER INFORMATION: n is a, c, g, t or u

<400> SEQUENCE: 9
gactggagtt cagacgtgtg ctcttccgat ctnnnnnnt                    39

<210> SEQ ID NO 10
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (33)..(38)
<223> OTHER INFORMATION: n is a, c, g, t or u

<400> SEQUENCE: 10
ctgacctcaa gtctgcacac gagaaggcta gannnnnn                     38

<210> SEQ ID NO 11
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: n is a, c, g, t or u

<400> SEQUENCE: 11
annnnnnaga tcggaagagc gtcgtgtagg gaaagagt                     38

<210> SEQ ID NO 12
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (32)..(37)
<223> OTHER INFORMATION: n is a, c, g, t or u

<400> SEQUENCE: 12
tgagaaaggg atgtgctgcg agaaggctag annnnnna                     38

<210> SEQ ID NO 13
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: n is a, c, g, t or u

<400> SEQUENCE: 13
tnnnnnntct agccttctcg cagcacatcc ctttcuca                     38
```

```
<210> SEQ ID NO 14
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: n is a, c, g, t or u

<400> SEQUENCE: 14
annnnnnaga tcggaagagc acacgtctga actccagtc                                    39

<210> SEQ ID NO 15
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: n is a, c, g, t or u

<400> SEQUENCE: 15
tnnnnnntct agccttctcg tgtgcagact tgaggtcag                                    39

<210> SEQ ID NO 16
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (33)..(38)
<223> OTHER INFORMATION: n is a, c, g, t or u

<400> SEQUENCE: 16
ctgaccycaa gtctgcacac gagaaggcta gannnnnna                                    39

<210> SEQ ID NO 17
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: n is a, c, g, t or u

<400> SEQUENCE: 17
annnnnnaga tcggaagagc acacgtctga actccagtc                                    39

<210> SEQ ID NO 18
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (33)..(38)
<223> OTHER INFORMATION: n is a, c, g, t or u

<400> SEQUENCE: 18
ctgacctcaa gtctgcacac gagaaggcta gannnnnna                                    39
```

```
<210> SEQ ID NO 19
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: n is a, c, g, t or u

<400> SEQUENCE: 19
tnnnnnntct agccaagagc cagcacatcc ctttcuca                              38

<210> SEQ ID NO 20
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (21)..(26)
<223> OTHER INFORMATION: n is a, c, g, t or u

<400> SEQUENCE: 20
acacgtctga atccagtcac nnnnnnatct cgtatgccgt cttctgcttg                  50

<210> SEQ ID NO 21
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (59)..(64)
<223> OTHER INFORMATION: n is a, c, g, t or u

<400> SEQUENCE: 21
aatgatacgg cgaccaccga gatctacacu ctttccctac acgacgctct tccgatctnn       60 nnnnt                                                                   65

<210> SEQ ID NO 22
<211> LENGTH: 71
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: n is a, c, g, t or u
<220> FEATURE:
<221> NAME/KEY: misc_feature
<222> LOCATION: (42)..(47)
<223> OTHER INFORMATION: n is a, c, g, t or u

<400> SEQUENCE: 22
annnnnnaga tcggaagagc acacgtctga actccagtca cnnnnnntag agcatacggc       60
agaagacgaa c                                                            71

<210> SEQ ID NO 23
<211> LENGTH: 65
<212> TYPE: DNA
<213> ORGANISM: Artificial Sequence
<220> FEATURE:
```

```
<223> OTHER INFORMATION: Primer
<220> FEATURE:
<221> NAME/KEY: misc_feature
<222> LOCATION: (59)..(64)
<223> OTHER INFORMATION: n is a, c, g, t or u

<400> SEQUENCE: 23
ttactatgcc gctggtggct ctagatgtga gaaagggatg tgctgcgaga aggctagann      60 nnnna                                                                  65

<210> SEQ ID NO 24
<211> LENGTH: 71
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (2)..(7)
<223> OTHER INFORMATION: n is a, c, g, t or u
<220> FEATURE:
<221> NAME/KEY: misc_feature
<222> LOCATION: (42)..(47)
<223> OTHER INFORMATION: n is a, c, g, t or u

<400> SEQUENCE: 24
tnnnnnntct agccttctcg tgtgcagact tgaggtcaga cnnnnnnatc tcgtatgccg      60
tcttctgctt g                                                           71
```

METHOD OF PRODUCING A NORMALISED NUCLEIC ACID LIBRARY USING SOLID STATE CAPTURE MATERIAL

FIELD OF THE INVENTION

The present invention relates to methods for preparing nucleic acids, more particularly methods for preparing nucleic acids for sequencing, particularly next generation sequencing and related methods such as genotyping-by-sequencing.

BACKGROUND OF THE INVENTION

The cost of DNA sequencing continues to fall, driven by ongoing improvements in sequencing technology. In the last few years, the cost per nucleotide of sequencing data has fallen by several orders of magnitude as the throughput, read length and sequence output of next-generation DNA sequencing (NGS) instruments has increased. It is now possible to process hundreds of thousands of millions of DNA templates in parallel, enabling the generation of sequencing data on a gigabase (Gb) scale. These advances in DNA sequencing technology have created a paradigm shift in scientific research and have opened unprecedented opportunities to investigate the genomes, methylomes and transcriptomes of organisms.

The increased ability to sequence, in a cost-effective manner, large numbers of individuals within the same species has altered the concept of variant discovery and genotyping in mapping studies, especially in plant species with complex genomes. Genotyping-by-sequencing (GBS), has emerged as a new technique, where the detection of sequence differences (namely SNPs) in a large segregating or mutant population is combined with scoring, thus allowing a rapid and direct study of its diversity targeted towards the mapping of a trait or a mutation of interest.

For many research applications, the sequence output generated by NGS instruments far exceeds the analysis requirements for a single sample. To address this problem, several methods have been developed for indexing of samples to enable multiple samples to be sequenced in parallel, and to allow for faster sample library preparation. For example, the recently introduced Nextra DNA Sample Prep Kit (Illumina) together with dual indexing (12×8 indices and two index reads) allows higher sample throughout for library preparation (Adey et al. 2010) and for pooling of up to 96 libraries.

However, one aspect of NGS that has not yet been fully addressed is the difficulty in accurately and easily partitioning sequence output across sample number and data density. Most current methods require accurate titration of individual sample libraries by qPCR prior to pooling to ensure the desired level of sequence coverage is achieved for each sample. Other methods attempt to achieve uniform sample representation in multiplexed libraries by accurate quantification of the amount of sample DNA used for library preparation. However, all current methods have limitations. For example, it is difficult to scale qPCR titration of individual sample libraries to large numbers of samples. Further, sample DNA quantification may still result in non-uniform sample representation in multiplexed libraries, due to differences between samples for efficacy at each library preparation step.

It is accordingly an object of the present invention to overcome, or at least alleviate, one or more of the deficiencies or difficulties related to the prior art.

In this specification, references to prior art are not intended to acknowledge or suggest that such prior art is part of the common general knowledge in Australia or that a person skilled in the relevant art could be reasonably expected to have ascertained, understood and regarded it as relevant.

SUMMARY OF THE INVENTION

Accordingly, in a first aspect of the present invention, there is provided a method of preparing a normalised nucleic acid library, said method including:
 providing
  one or more nucleic acid samples, and
  one or more samples of solid state capture material;
 contacting each nucleic acid sample with a sample of capture material to provide, captured nucleic acid samples; and
 pooling the captured nucleic acid samples to provide the normalised nucleic acid library.

Applicants have found that the present method is particularly suitable for normalising nucleic acid sample libraries for sequencing, such as next-generation sequencing, especially genotyping-by-sequencing.

The method may be applied to a single sample or to a plurality of nucleic acid samples using a plurality of samples of solid state capture material.

By 'normalised', as used herein, is meant that the amount of each nucleic acid sample in the library is controlled or predetermined. Preferably, each nucleic acid sample is substantially uniformly represented in the library. Alternatively, the nucleic acid samples may be present in the library in different, predetermined concentrations. This may be achieved by capturing nucleic acid samples to different amounts of capture material or by pooling different amounts of the captured nucleic acids.

By 'nucleic acid', as used herein, is meant a chain of nucleotides capable of carrying genetic information. The term generally refers to genes or functionally active fragments or variants thereof and or other sequences in the genome of the organism that influence its phenotype. The term 'nucleic acid' includes DNA (such as cDNA or genomic DNA) and RNA (such as mRNA or microRNA) that is single- or double-stranded, optionally containing synthetic, non-natural or altered nucleotide bases, synthetic nucleic acids and combinations thereof.

By a nucleic acid 'library', as used herein, is meant is a collection of nucleic acid molecules. In this context the nucleic acid library is preferably a multiplexed nucleic acid library, where the representation of individual nucleic acid samples in the library is determined by the pooled amount of captured nucleic acid for each sample.

The solid state capture material may be of any suitable type that provides a known binding capacity, resulting in a substantially constant amount of captured DNA per fixed amount of capture material. In a preferred embodiment the capture material may be streptavidin. In a preferred embodiment the solid state capture material may include streptavidin-coated beads, more preferably streptavidin-coated magnetic beads.

In an embodiment where streptavidin is used as a capture material, the nucleic acids may be biotinylated to facilitate binding of the nucleic acids to the capture material.

In a preferred embodiment, an excess of nucleic acid may be contacted with a fixed amount of solid state capture material to facilitate substantial saturation of the binding capacity of the capture material, and consequently the capture of a substantially constant amount of captured DNA per fixed amount of capture material.

In a preferred embodiment, the captured nucleic acid samples may be washed to substantially remove unbound nucleic acids from the samples or minimise their presence in the samples.

The captured nucleic acid samples may then be pooled or combined, and preferably the captured nucleic acids are eluted, to generate the nucleic acid library. The representation of individual samples within the nucleic acid library may be adjusted by varying the pooled amount of solid state captured nucleic acid for each sample.

In a preferred embodiment, the amount of each nucleic acid sample in the library may be substantially uniformly represented in the library. In an alternate preferred embodiment, the nucleic acid samples may be present in the library in different, predetermined concentrations by capturing the nucleic acid samples to different, predetermined amounts of capture material or by pooling different amounts of the captured nucleic acids.

In a further preferred embodiment, the method of the present invention may be automated, for example it may be performed by a liquid handling robot.

The nucleic acid library so generated may be suitable for sequencing utilising techniques such as next-generation sequencing and related methods such as genotyping-by-sequencing.

By 'next-generation sequencing (NGS)', as used herein, is meant high-throughput sequencing where the sequencing process is performed in parallel, for example producing thousands or millions of sequences at once.

By 'genotyping-by-sequencing' is meant detection of sequence differences or single nucleotide polymorphisms (SNPs) by next-generation sequencing techniques.

In a preferred embodiment, the nucleic acid library may be amplified, for example by polymerase chain reaction (PCR), and titrated using standard methods prior to NGS or GBS.

Accordingly, the present invention provides use of a method according to the present invention in next-generation sequencing or genotyping-by-sequencing.

The present invention also provides a method of next generation sequencing or genotyping-by-sequencing, said method including preparing a normalised nucleic acid library by a method according to the present invention, amplifying and/or titrating the nucleic acid library and then performing next-generation sequencing or genotyping-by-sequencing.

While applicants do not wish to be limited by the following, one or more advantages of the method of the present invention over other prior art sample normalisation methods, include its ability to be scaled up for the processing of, for example, thousands of samples; its amenity to automation, for example on a liquid handling robot; its compatibility with most NGS sequencing sample library preparation methods; its ability to be integrated into workflows for the analysis of genomes, methylomes and transcriptomes; its ability to generate a user-defined amount of sequencing output for each pooled sample in a multiplexed library; and its ability to enable flexibility and control for the generation of sequencing output across sample number and data density.

In a further aspect of the present invention there is provided a nucleic acid library produced by the method of the present invention.

DETAILED DESCRIPTION OF THE PREFERRED EMBODIMENTS

Overview of Preferred Embodiment BeadPlex

An example of the method of the present invention has been designated BeadPlex. BeadPlex is a simple method for normalising sample libraries, for example in preparation for next-generation sequencing. It may be based on the simplicity of solid-state streptavidin capture of biotinylated DNA samples. For example, an excess of DNA fragments may be incubated with a fixed amount of streptavidin-coated magnetic beads to ensure that the binding capacity of the beads is saturated and a constant amount of sample DNA is immobilised (FIG. 1a). Following stringent washing to remove unbound molecules, the magnetic beads from individual samples are pooled and the immobilised DNA may be eluted to generate a multiplexed sample library. The representation of individual samples within the multiplexed library may be adjusted by varying the pooled amount of bead captured DNA for each sample (FIG. 1b). The above-mentioned steps may be easily automated on a liquid handling robot. Next, the multiplexed library may be amplified by PCR and titrated via standard methods before loading on a next-generation DNA sequencing instrument.

Figures 2A, 2B:
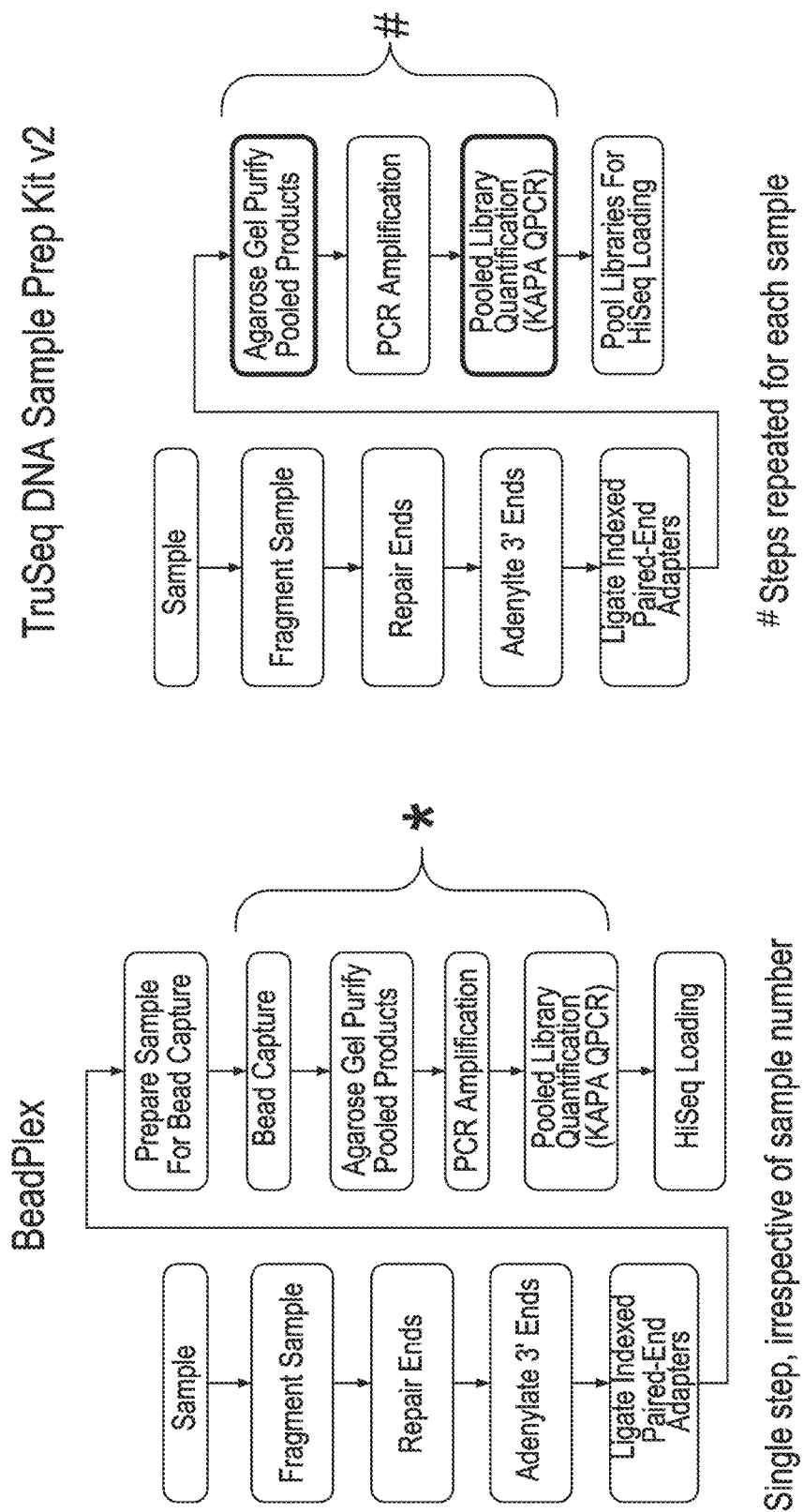

One or more advantages of the BeadPlex embodiment include its compatibility with existing library preparation methods for short-read next-generation DNA sequencers such as the Illumina HiSeq2000. It may be seamlessly integrated into existing protocols used to prepare sample libraries for DNA, RNA and PCR amplicons. BeadPlex may provide significant time- and cost-savings for the processing of multiple samples by eliminating the requirement for size selection and qPCR quantification of individual samples (FIG. 2). The ability to adjust the representation of individual samples within a BeadPlex library, via pooling different amounts of bead captured DNA, provides flexibility for the generation of the same or a different amount of sequence output for each sample pooled in a single sequencing lane, thereby providing effective control of sequence output across sample number and data density. BeadPlex is highly scalable; it may be applied to a single sample, or many samples.

Implementation of BeadPlex

BeadPlex may be used to normalise sample libraries prepared from a range of starting templates including DNA, RNA and PCR amplicons. Preferably, BeadPlex is performed immediately after DNA molecules, suitable for loading onto a next-generation sequencer, are formed. This facilitates competent molecules being normalised with BeadPlex and helps minimise the number of subsequent sample handling steps by pooling multiple samples as soon as possible.

For genomic DNA, samples are typically sheared to short fragments and end-repaired for subsequent ligation to biotinylated adapter molecules. The adapter molecules may be fully or partially double-stranded, and may contain individual barcodes for sample tracking. Partially double-stranded (Y-junction) adapters are preferred, as they help ensure that both sample DNA fragment strands have the correct adapter sequence at each end. The adapter molecules may contain PCR priming sites that allow for an optional pre-capture amplification step to increase the abundance of sample DNA, or to introduce additional barcodes for sample tracking via specific tailed oligonucleotide primers (FIG. 3). The combination of internally barcoded adapters and introduction of an additional (external) barcode via PCR (either before or after sample pooling) allows an almost unlimited number of samples to be pooled and sequenced in the same lane (FIG. 4). Following removal of unligated adapter and incompetent sample DNA molecules with partially ligated adapters (eg. by Exonuclease III digestion), the samples are normalised using BeadPlex.

For RNA, reverse transcription and cDNA synthesis may be used to generate double-stranded cDNA as starting template for sample library preparation. The double-stranded cDNA may be prepared using a range of methods including random priming and PCR amplification, and is suitable for subsequent ligation to biotinylated adapter molecules and BeadPlex sample normalisation (as described above).

The steps required to prepare a normalised sample library for PCR amplicons depends on whether the amplicons are already competent for next-generation DNA sequencing. Competent PCR amplicons are typically generated via amplification using specific tailed oligonucleotide primers, and may be immediately utilised for BeadPlex sample normalisation when biotinylated. Incompetent PCR amplicons may be readied for next-generation DNA sequencing via a few PCR cycles using specific tailed primers, one of which is biotinylated. Alternatively, an adapter molecule may be ligated to the amplicons (as described previously).

The present invention will now be more fully described with reference to the following examples. However, it should be understood that, the examples are illustrative only and should not be taken in any way as a restriction of the present invention as described above.

IN THE FIGURES

FIG. 1. Preparation of a BeadPlex library of normalised samples. (a) Excess biotinylated DNA for each sample is incubated with a fixed amount of streptavidin-coated magnetic beads. Unbound DNA is removed by washing, leaving a constant amount of captured DNA. (b) Bead captured DNA from individual samples is pooled and eluted to generate a multiplexed library. The representation of individual samples may be manipulated by varying the pooled amount of captured DNA for each sample.

FIG. 2. Seamless integration of BeadPlex into the Illumina TruSeq protocol for preparing genomic DNA samples for next-generation sequencing. Time and cost savings afforded by BeadPlex for the processing of multiple samples is illustrated.

FIG. 3. Sequences of adapters and primers used for pre-capture and post-capture PCR amplification in BeadPlex.

(a) Double-stranded adapter designs:
mpxPE1supp Primer—SEQ ID NO: 1; mpxPE1 Primer—SEQ ID NO: 2, gbsPE1 Primer—SEQ ID NO: 3; mpxPE1ds.adp(+)—SEQ ID NO: 4; mpxPE1ds.adp(−)—SEQ ID NO: 5; mpxPE2supp Primer—SEQ ID NO: 6; mpxPE2 Primer—SEQ ID NO: 7; gbsPE2 Primer—SEQ ID NO: 8; mpxPE2ds.adp(+)—SEQ ID NO: 9; mpxPE2ds.adp(−)—SEQ ID NO: 10. The remaining sequences are primers linked to unknown sequences of any length (xxxxxxxxxx)—SEQ ID NOS: 4, 11, 12 and 13 (first example); SEQ ID NOS: 4, 14, 12 and 15 (second example); SEQ ID NOS: 9, 14, 16 and 15 (third example).

[1]Double-stranded adapter sequences are shown in underline and double underline. Index sequences for adapter barcoding are shown by a line above the sequence.

[2]Biotin-gbsPE1 and gbsPE2 primers are used in pre-capture PCR when external indexing for sample tracking is not required.

[3]Biotin-mpxPE1 and mpxPE2 primers are used in pre-capture PCR when external indexing for sample tracking is required. Index sequence for external barcoding is shown by a double line above the sequence.

[4]gbsPE1 and gbsPE2 primers are used in post-capture PCR when external indexing for sample tracking is not required.

[5]mpxPE1supp and mpxPE2supp primers are used in post-capture PCR when external indexing for sample tracking is required.

[6]Only half of the adapter-ligated sample DNA fragments have the correct adapter sequence configuration (mpxPE1-mpxPE2) for next-generation DNA sequencing.

[7]The asterisk * represents a phosphorothioate modification.

(b) Y-junction adapter designs:
mpxPE1supp Primer—SEQ ID NO: 1; mpxPE1 Primer—SEQ ID NO: 2, gbsPE1 Primer—SEQ ID NO: 3; mpxPEy.adp(+)—SEQ ID NO: 4; mpxPEy.adp(−)—SEQ ID NO: 10; gbsPE2_Primer—SEQ ID NO: 8; mpxPE2_Primer—SEQ ID NO: 7; mpxPE2supp_Primer—SEQ ID NO: 6. The remaining sequences are primers linked to unknown sequences of any length (xxxxxxxxxx)—SEQ ID NOS: 4, 17, 18 and 19.

[1]Double-stranded portion of Y-junction adapter sequences is shown in triple underline. The mpxPE1 and mpxPE2 portions are shown in underline and double underline, respectively. Index sequences for adapter barcoding are shown by a line above the sequence.

[2]Biotin-gbsPE1 and gbsPE2 primers are used in pre-capture PCR when external indexing for sample tracking is not required.

[3]Biotin-mpxPE1 and mpxPE2 primers are used in pre-capture PCR when external indexing for sample tracking is required. Index sequence for external barcoding is shown by a double line above the sequence.

[4]gbsPE1 and gbsPE2 primers are used in post-capture PCR when external indexing for sample tracking is not required.

[5]mpxPE1supp and mpxPE2supp primers are used in post-capture PCR when external indexing for sample tracking is required.

[6]Every adapter-ligated sample DNA fragment has the correct adapter sequence configuration (mpxPE1-mpxPE2) for next-generation DNA sequencing.

[7]The asterisk * represents a phosphorothioate modification.

FIG. 4. Sample tracking using internal and external barcode sequences.

(a) Internally barcoded adapters provide X*Y index combinations for sample tracking. The example shows primers linked to unknown sequences of any length (xxxxxxxxxx)—SEQ ID NOS: 4, 14, 12 and 15.

(b) Internally barcoded adapters used in combination with an external barcode introduced via PCR provides $(X*Y)^Z$ combinations for sample tracking. The examples show primers linked to unknown sequences of any length (xxxxxxxxxx)—SEQ ID NOS: 2, 4, 14, 12, 15 and 20 (first example); SEQ ID NOS: 21, 22, 23 and 24 (second example).

Figure 5:
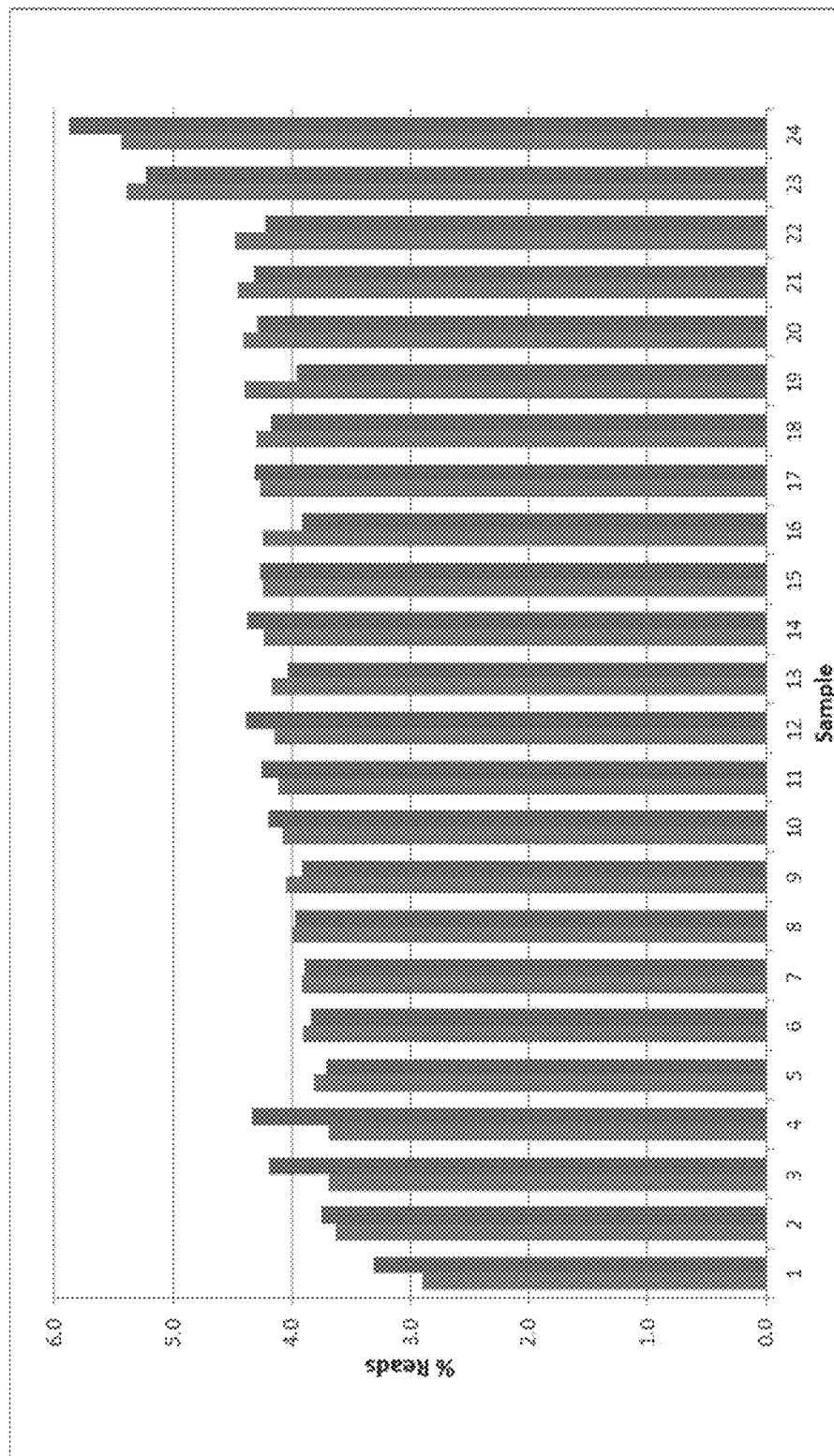

FIG. 5. Sample representation in 24-plex BeadPlex libraries. Sample normalisation was performed by (a) directly incubating 1 µg of biotinylated DNA for each sample with MyOne™ bead (left hand, lighter grey bars), and (b) incubating biotinylated DNA generated for each sample after seven cycles of pre-capture PCR (right hand, darker grey bars).

Figure 6:
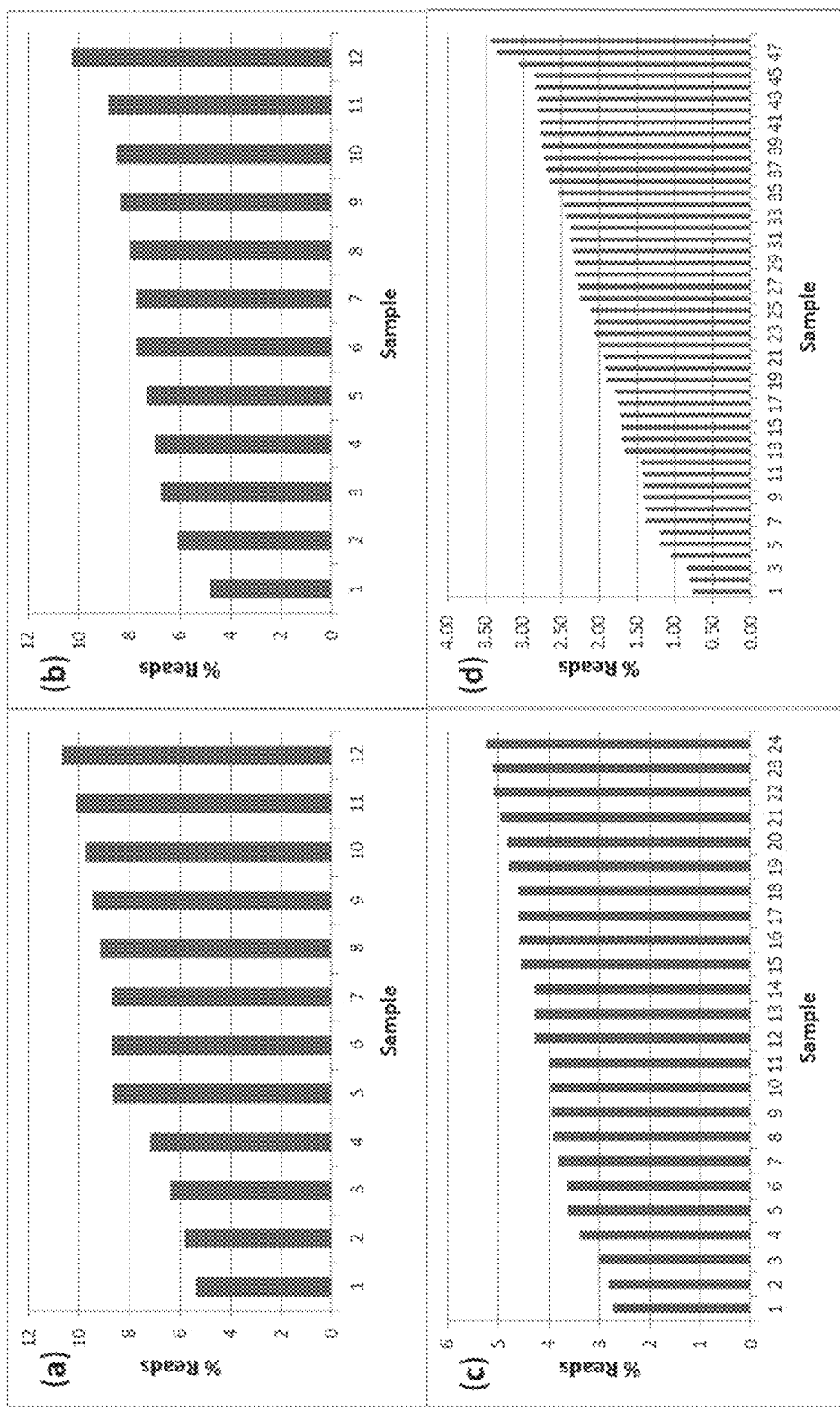

FIG. 6. Sample representation in first (a) and second (b) 12-plex libraries, 24-plex library (c) and 48-plex library (d). Sample normalisation was performed by incubating biotinylated DNA generated for each sample after seven cycles of pre-capture PCR.

Figure 7:
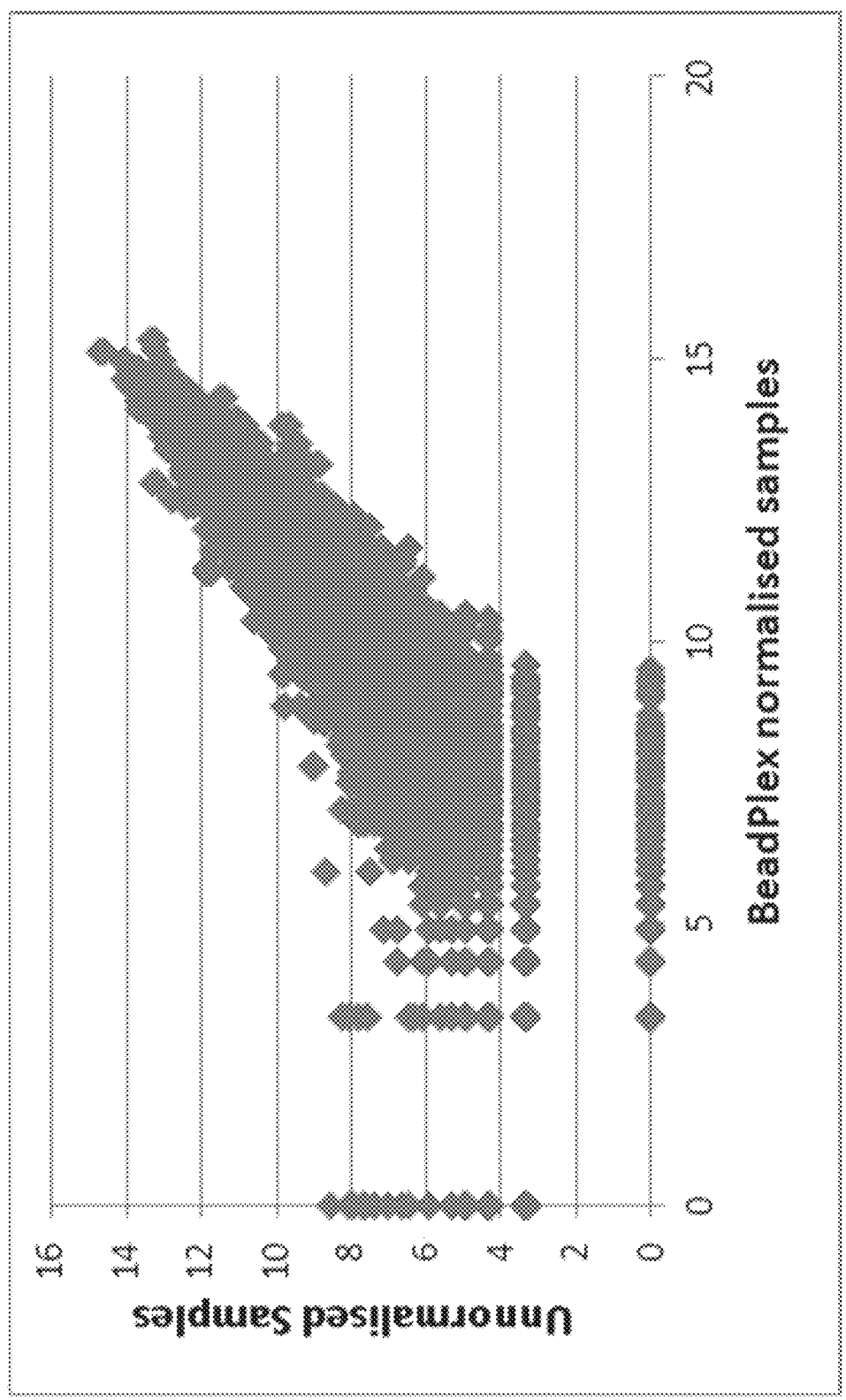

FIG. 7. $\text{Log}_2$ plot of the number of reads mapped to contig sequences for the pooled amplicons used as input DNA for sample library preparation. Shown is the sequence coverage distribution for the 24 samples in the unnormalised, and two 12-plex and one 24-plex normalised libraries.

FIG. 8. Two rate limiting steps for processing large sample numbers.

Figure 9:
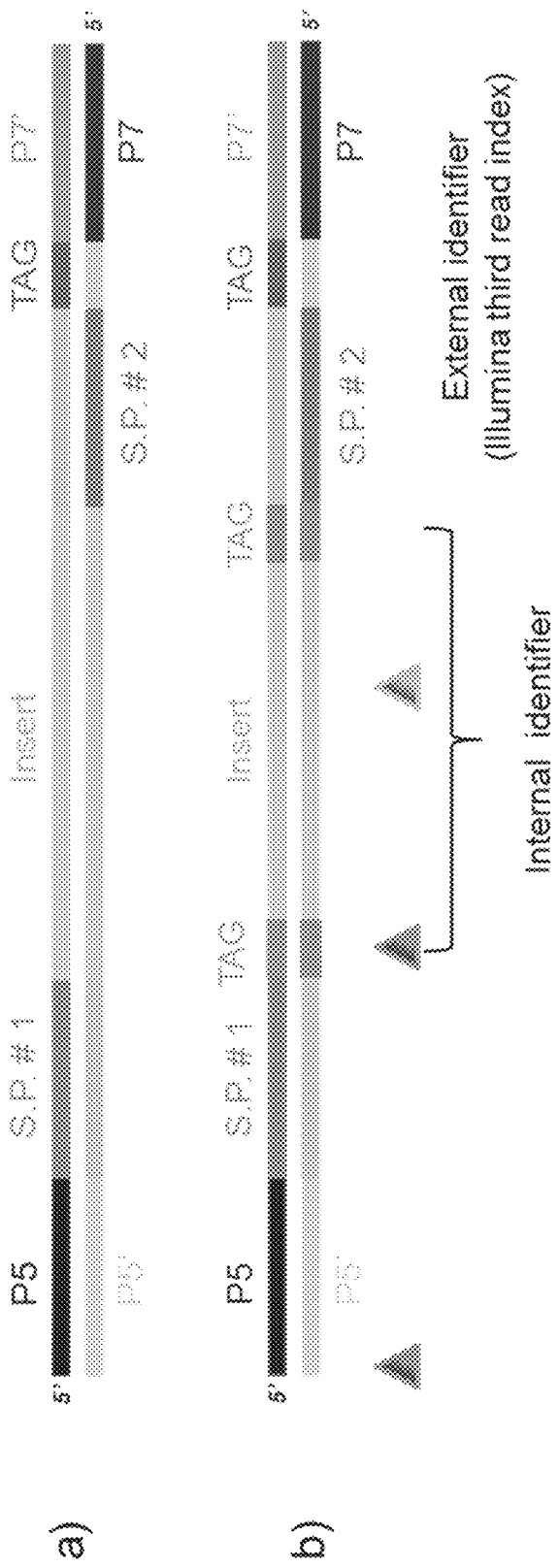

FIG. 9. (a) External configuration "Standard Illumina method" (X combinations). (b) Internal-external configuration "BeadPlex method" (X times Y combinations).

Figure 10:
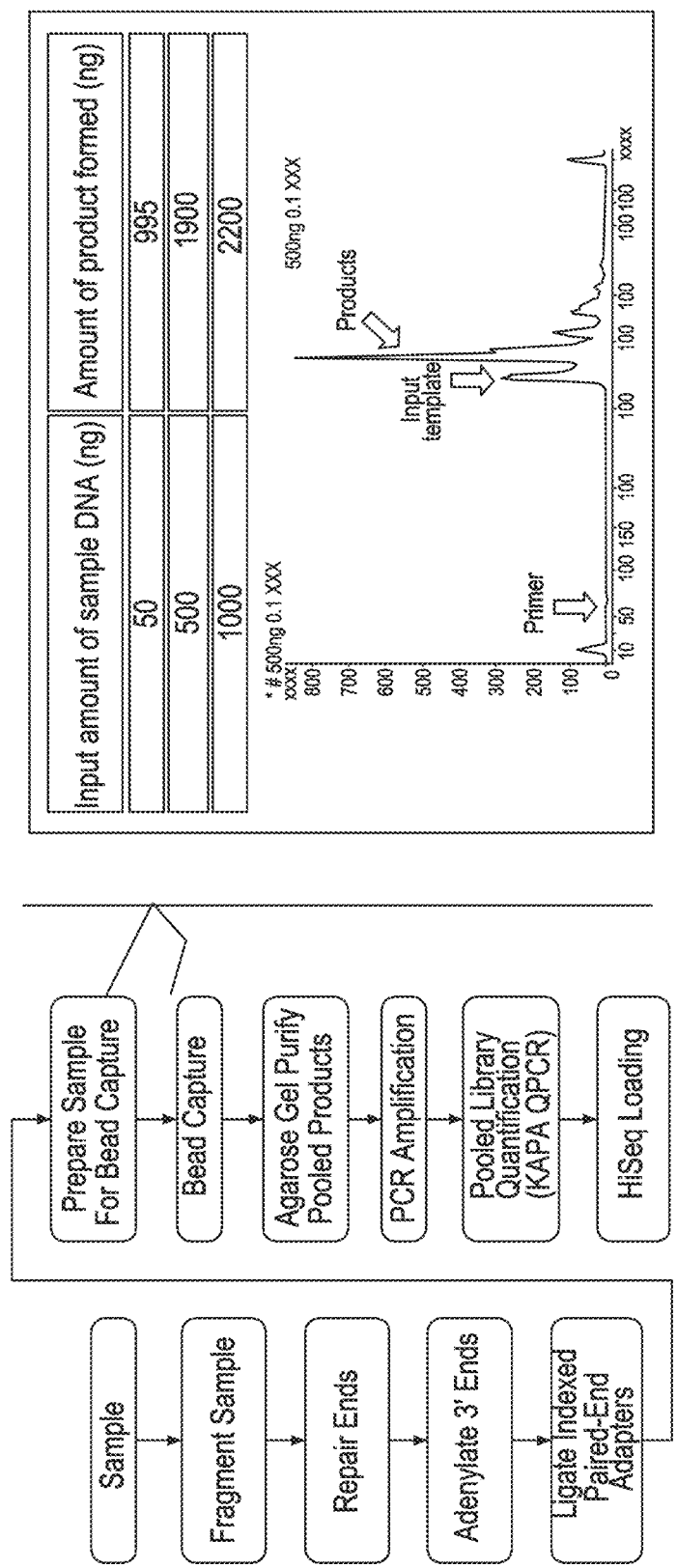

FIG. 10. Minimal effect of input amount of sample DNA on capture efficiency.

Figure 11:
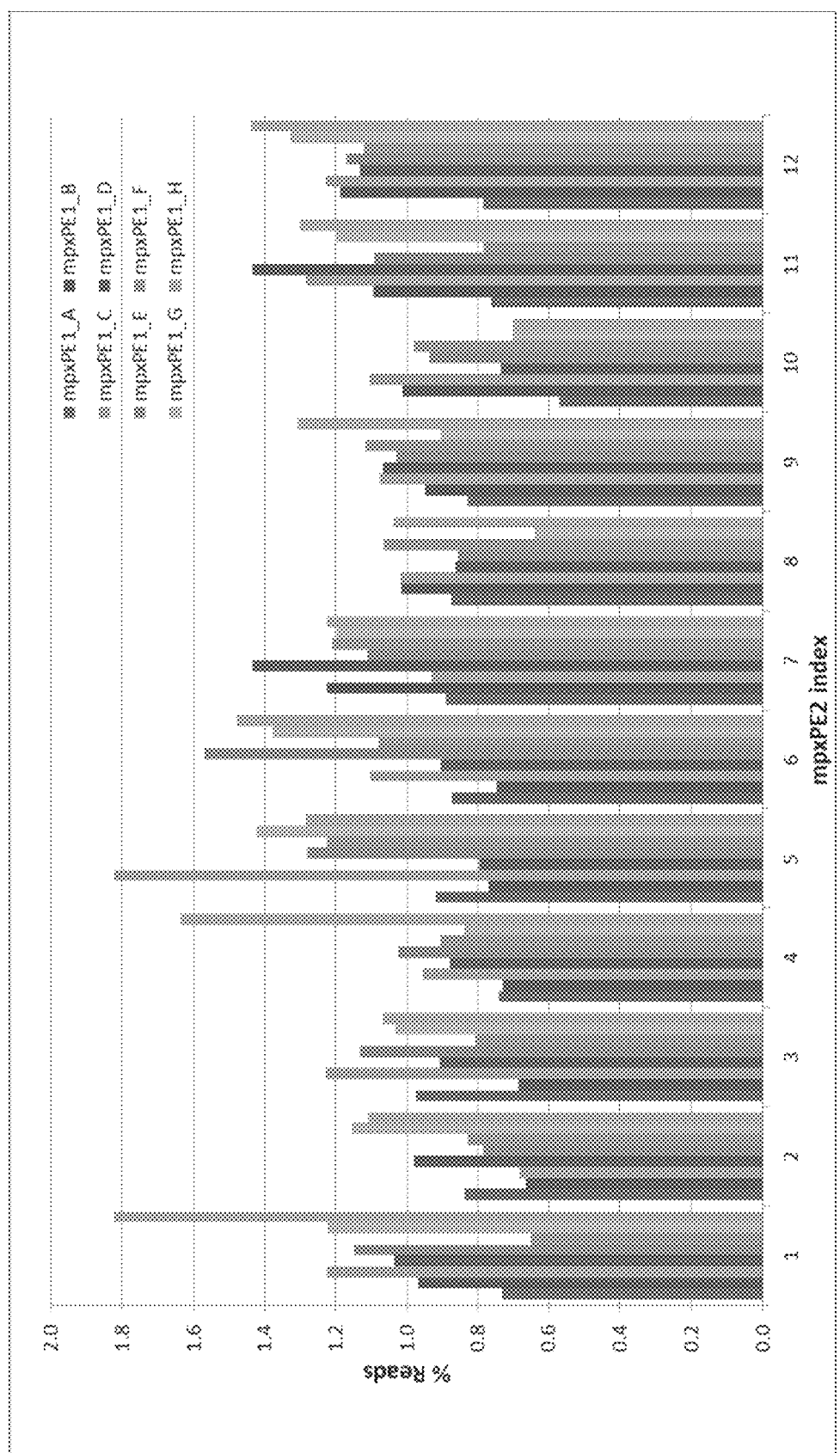

FIG. 11. Similar representation of samples in HiSeq sequence output. 1×96-plex (% CV #24.5)—post DNA capture step. Each group of reads is for, from left to right, mpxPE1_A, mpxPE1_B, mpxPE1_C, mpxPE1_D, mpxPE1_E, mpxPE1_F, mpxPE1_G, mpxPE1_H.

EXAMPLE 1

BeadPlex Method Optimisation

A series of pilot experiments based on real-time PCR were initially performed to investigate and optimise key parameters for BeadPlex methodology.
Biotinylated DNA to Streptavidin-Coated Magnetic Bead Ratio The ability to normalise a sample library by solid-state streptavidin capture of biotinylated DNA relies on saturation of the binding capacity of the solid-state substrate to ensure a constant amount of DNA is immobilised for each sample. To determine the fold excess of biotinylated DNA required to saturate a given amount of MyOne™ streptavidin-coated magnetic beads, we incubated 1 µg of a 125-bp biotinylated PCR product in triplicate with sufficient MyOne™ beads to theoretically bind 500, 250, 125 and 62.5 ng of biotinylated fragments. This corresponded to a 2, 4, 8 and 16-fold excess of biotinylated DNA, respectively. The choice of 1 µg biotinylated DNA input was based on the typical yield of genomic DNA from a standard Illumina TruSeq library preparation method following sample fragmentation, end repair and adapter ligation. Following incubation, the magnetic beads were washed to remove unbound DNA molecules and the immobilised DNA were released by heat elution, diluted four-fold and assessed by qPCR to determine the recovery yield.

Analysis of variance of the $Ct_{50}$ values (the number of cycles required to reached 50% of total fluorescence) for the triplicated samples for each DNA-to-bead ratio showed no significant differences (p=0.218). The average difference in $Ct_{50}$ value between any pairwise comparisons of samples was 0.42, suggesting that the recovery of biotinylated fragments was similar, at least within the detection limits of the qPCR assay. The coefficient of variation (CV) for each DNA-to-bead ratio was relatively low (Table 1), suggesting high reproducibility for the amount of DNA immobilised. The CV tended to decrease (up to 6-fold) with increasing DNA-to-bead ratio, implying that a higher excess of biotinylated DNA may provide for more uniform capture across samples. Overall, the data indicated that at least a two-fold excess of biotinylated DNA was sufficient to ensure repeatable recovery of the same (or a very similar) amount of sample DNA for downstream processing.

TABLE 1

$Ct_{50}$ values for qPCR amplification of recovered DNA following capture of 1 µg of biotinylated DNA to MyOne™ streptavidin-coated magnetic beads with different theoretical binding capacities. qPCR assays for each replicate capture reaction at each DNA-to-bead ratio were performed in triplicate.

| MyOne™ bead DNA binding capacity | DNA fold excess | Capture Reaction | $Ct_{50}$ | Average $Ct_{50}$ | CV (%) |
|---|---|---|---|---|---|
| 500 ng | 2x | 1 | 12.24 | 11.32 | 8.12 |
|  |  | 2 | 11.33 |  |  |
|  |  | 3 | 10.40 |  |  |
| 250 ng | 4x | 1 | 11.61 | 10.89 | 8.27 |
|  |  | 2 | 9.88 |  |  |
|  |  | 3 | 11.18 |  |  |
| 125 ng | 8x | 1 | 12.83 | 12.47 | 5.35 |
|  |  | 2 | 12.88 |  |  |
|  |  | 3 | 11.70 |  |  |
| 62.5 ng | 16x | 1 | 11.87 | 12.06 | 1.39 |
|  |  | 2 | 12.17 |  |  |
|  |  | 3 | 12.15 |  |  |

Effect of Input DNA Size (qPCR)

The binding capacity for solid-state streptavidin capture of biotinylated DNA is inversely related to the molecule size, with larger DNA fragments showing reduced binding capacity due to steric hindrance at the substrate surface. To investigate the effect of DNA molecule size on the binding capacity of MyOne™ streptavidin-coated magnetic beads, we incubated 1 µg of biotinylated PCR product of varying size with a fixed amount of MyOne™ beads. The theoretical binding capacity of the MyOne™ beads was 62.5 ng biotinylated DNA, which provided a 16:1 DNA-to-bead ratio. The biotinylated PCR products were of size 125, 325-375, 375-425 and 525-575-bp, respectively. Each streptavidin capture reaction was performed with five technical replicates. The choice of DNA fragment sizes was based on those typically used in standard Illumina library preparation methods. Following incubation, the magnetic beads were washed to remove unbound DNA and the immobilised fragments were released by heat elution, diluted 10-fold and assessed by qPCR to determine the recovery yield.

Analysis of variance of the $Ct_{50}$ values showed a significant (p>0.0001) effect of DNA fragment size on the binding capacity of MyOne™ beads. $Ct_{50}$ values for the shortest DNA fragments were on average four PCR cycles lower than for the largest sized molecules, indicating up to a 16-fold difference in bead binding capacity (Table 2). However, the CV for each DNA fragment size range was small (<7%) implying high repeatability for the amount of DNA immobilised. Overall, these results indicate sample DNA fragment size does not impact on the repeatability for the amount of DNA captured. However, the data does indicate the amount of MyOne™ beads will need to be increased for larger sized fragments to ensure sufficient DNA is captured to enable the sample library to be amplified with a total number of PCR cycles that falls within the recommended optimal range, typically less than 16 cycles for most current next-generation sequencing library preparation methods.

TABLE 2

$Ct_{50}$ values for qPCR amplification of recovered DNA following capture of 1 µg of biotinylated DNA of varying size to a fixed amount of MyOne™ streptavidin-coated magnetic beads. qPCR assays for each replicate capture reaction with each DNA fragment size were performed in triplicate.

| DNA fragment size | Capture Reaction | $Ct_{50}$ | Average $Ct_{50}$ | CV (%) |
|---|---|---|---|---|
| 125 bp | 1 | 12.26 | 12.10 | 2.29 |
|  | 2 | 11.90 |  |  |
|  | 3 | 12.27 |  |  |
|  | 4 | 11.72 |  |  |
|  | 5 | 12.36 |  |  |
| 325-375 bp | 1 | 13.43 | 12.83 | 3.39 |
|  | 2 | 12.25 |  |  |
|  | 3 | 12.93 |  |  |
|  | 4 | 12.91 |  |  |
|  | 5 | 12.62 |  |  |
| 375-425 bp | 1 | 13.75 | 13.25 | 3.52 |
|  | 2 | 13.76 |  |  |
|  | 3 | 12.95 |  |  |
|  | 4 | 12.96 |  |  |
|  | 5 | 12.82 |  |  |
| 425-525 bp | 1 | 17.80 | 16.50 | 6.05 |
|  | 2 | 15.77 |  |  |
|  | 3 | 15.75 |  |  |
|  | 4 | 17.35 |  |  |
|  | 5 | 15.81 |  |  |
| 525-575 bp | 1 | 15.73 | 16.28 | 6.84 |
|  | 2 | 16.40 |  |  |
|  | 3 | 16.62 |  |  |
|  | 4 | 14.82 |  |  |
|  | 5 | 17.83 |  |  |

Pre-capture PCR

PCR amplification of sample libraries prior to solid-state streptavidin capture enables the processing of samples for which limited DNA is available. It also allows for the introduction of individual barcodes via specific tailed oligonucleotides for downstream sample tracking. To optimise conditions for pre-capture PCR, we performed seven cycles of amplification on non-biotinylated DNA fragments (with a size range of 325-375 bp) using 0.2 µM of biotinylated oligonucleotide primers. Pre-capture PCR assays were performed in triplicate using different amounts of DNA template: 50, 250, 500, 750 and 1000 ng, respectively. Following SPRI purification to remove unincorporated primers, the biotinylated pre-capture amplification products were incubated with MyOne™ beads providing a theoretical binding capacity of 62.5 ng biotinylated DNA. After bead washing to remove unbound fragments, the immobilised DNA was released by heat elution, diluted four-fold and assessed by qPCR to determine the recovery yield.

Analysis of variance showed that varying the amount of DNA input in the pre-capture PCR had no significant effect (p=0.75) on the normalisation efficiency of MyOne™ beads. The average difference in $Ct_{50}$ between any pairwise comparisons of DNA inputs was less than 1 cycle, suggesting as little as 50 ng of DNA template in the pre-capture PCR was adequate to generate sufficient biotinylated product to saturate the bead binding capacity. The CV were less than 9% for all DNA input amounts (Table 3). Moreover, only about nine cycles of pre-capture PCR was required to reach $Ct_{50}$, regardless of DNA input. These results indicate that even when starting with limited (at least 50 ng) non-biotinylated DNA template, the total number of PCR cycles required for pre- and post-capture amplification of a sample library will fall within the range typically recommended (<16 cycles) for most current next-generation sequencing library preparation methods.

TABLE 3

$Ct_{50}$ values for qPCR amplification of recovered DNA following immobilisation of biotinylated pre-capture PCR product amplified from varying amounts of non-biotinylated DNA as input template. qPCR assays for each replicate capture reaction were performed in triplicate.

| Amount of input DNA in pre-capture PCR | Capture Reaction | $Ct_{50}$ | Average $Ct_{50}$ | CV (%) |
|---|---|---|---|---|
| 50 ng | 1 | 8.98 | 8.91 | 4.09 |
|  | 2 | 9.24 |  |  |
|  | 3 | 8.52 |  |  |
| 250 ng | 1 | 8.32 | 8.60 | 2.96 |
|  | 2 | 8.65 |  |  |
|  | 3 | 8.82 |  |  |
| 500 ng | 1 | 8.62 | 8.66 | 3.54 |
|  | 2 | 8.98 |  |  |
|  | 3 | 8.37 |  |  |
| 750 ng | 1 | 8.59 | 8.62 | 0.57 |
|  | 2 | 8.68 |  |  |
|  | 3 | 8.60 |  |  |
| 1000 ng | 1 | 8.23 | 8.96 | 8.96 |
|  | 2 | 9.82 |  |  |
|  | 3 | 8.83 |  |  |

To further confirm sufficient biotinylated product was generated during pre-capture PCR for efficient sample normalisation, we performed a series of pre-capture PCR assays using 50, 500 and 1000 ng of a non-biotinylated 300-bp DNA fragment as template and 0.05, 0.10 and 0.20 µM of biotinylated oligonucleotide primers. The PCR products were purified by ethanol precipitation and analysed on an Aligent BioAnalyser™ using a DNA1000 chip to quantify the amount of product formed. The yield of PCR product was determined from the ratio of the peak areas corresponding to the PCR product and input template (i.e. yield=peak area of PCR product/peak area of input template * ng amount of input template).

Comparison of the pre-capture PCR yields showed that about 1 µg of biotinylated product could be generated from as low as 50 ng of DNA template in reactions performed using 0.10 µM of oligonucleotide primer. At least 500 ng of DNA template was required in pre-capture reactions performed using 0.05 µM primer (Table 4). These results show that seven cycles of pre-capture PCR performed with at least 0.1 µM primer generates sufficient biotinylated product for efficient sample normalisation.

TABLE 4

Average yield of biotinylated product generated in seven cycles of pre-capture PCR using varying amounts of non-biotinylated DNA as input template and different concentrations of oligonucleotide primers.

| Amount of input DNA in pre-capture PCR | Amount of PCR product formed (ng) | | |
|---|---|---|---|
|  | 0.2 µM | 0.1 µM | 0.05 µM |
| 50 ng | 1210 | 995 | 595 |
| 500 ng | 2750 | 1900 | 1200 |
| 1000 ng | 3100 | 2200 | 1200 |

Repeatability from Independent Samples (qPCR)

To confirm key parameters for BeadPlex were optimised before moving to method validation using next-generation sequencing, we investigated the repeatability of bead capture across six independent assays using genomic DNA as template. One µg of genomic DNA was fragmented to an average size of 300-bp using a Covaris instrument, end-repaired, adenylated and ligated to a non-biotinylated double-stranded adapter. Seven cycles of pre-capture PCR was performed using the entire amount of adapter-ligated DNA as input template and 0.1 µM of biotinylated oligonucleotide primers. The pre-capture PCR products were purified by SPRI to remove unincorporated primer and incubated with MyOne™ beads with a theoretical binding capacity of 62.5 ng biotinylated DNA. After bead washing to remove unbound fragments, the immobilised DNA was released by heat elution, diluted 10-fold and assessed by qPCR to determine the recovery yield.

The Ct50 values among the six independent samples were similar. The average number of cycles required to achieve $Ct_{50}$ was 8.93±0.22 (Table 5). These results confirm that sufficient biotinylated pre-capture product was formed for effective sample normalisation, and that the recovered amount of normalised sample DNA was adequate to ensure that the total pre- and post-capture PCR cycle number fell within the optimal range recommended in most next-generation sequencing library preparation methods.

TABLE 5

$Ct_{50}$ values for qPCR amplification of recovered DNA from immobilisation of biotinylated pre-capture PCR product amplified from six independently prepared genomic DNA samples. qPCR assays for each replicate capture reaction were performed in triplicate.

| Capture Reaction | $Ct_{50}$ | Average $Ct_{50}$ | CV (%) |
|---|---|---|---|
| 1 | 8.25 | 8.93 | 5.88 |
| 2 | 8.40 | | |
| 3 | 8.88 | | |
| 4 | 9.31 | | |
| 5 | 9.60 | | |
| 6 | 9.13 | | |

EXAMPLE 2

BeadPlex Method Validation

Evenness (Uniformity) of Sequence Coverage

A limitation of qPCR for optimising key parameters for BeadPlex is detection sensitivity, since each cycle of amplification theoretically represents a two-fold change in the number of DNA molecules. In contrast, next-generation sequencing enables precise quantification of the abundance of DNA molecules by virtue of sequence read counts. To determine if the BeadPlex parameters investigated in the pilot experiments using qPCR translated into robust normalisation of sample libraries when next-generation sequenced, we performed a series of experiments to assess the evenness (or uniformity) of sequence coverage across samples in BeadPlex-prepared libraries.

In the first experiment, the uniformity of sample capture to MyOne™ beads was re-examined by preparing a pool of 24 samples for next-generation sequencing. One µg of biotinylated DNA was prepared for each sample by PCR amplification of the same 300-bp fragment using biotinylated PE1 primer and a different indexed PE2 primer. The use of a different indexed PE2 primer for each sample allowed the tracking of sequence reads from individual samples. The biotinylated DNA fragments were incubated with MyOne™ beads providing a theoretical binding capacity of 62.5 ng of biotinylated DNA. After washing to remove unbound fragments, the MyOne™ beads for the 24 samples were pooled and the captured DNA was released by heat elution. The released DNA was post-capture PCR amplified, quantified by qPCR and loaded in a single lane on the HiSeq2000 instrument as a 5% spike (by volume). The percentage of indexed reads generated per sample was used to assess the uniformity of sample capture to MyOne™ beads.

The proportion of sequence reads attributed to each of the 24 samples is shown in FIG. 5a. The average coverage across samples was 4.17±0.15%, which approached the theoretical expectation for uniform sequence coverage across the 24 samples (Table 6). 92% (22/24) of samples had a read coverage within a factor of 1.2 of the median. The CV was 0.12. These findings were consistent with results from the qPCR analyses performed in the pilot experiments and confirm that streptavidin-coated MyOne™ beads capture a constant amount of biotinylated product, and allow for effective sample normalisation.

TABLE 6

Sample representation in 24-plex BeadPlex library.

| Sample | PE2 index | Number of reads | % Reads |
|---|---|---|---|
| 1 | GCGAGC | 985,308 | 2.91 |
| 2 | GATCAG | 1,231,496 | 3.63 |
| 3 | TGCTGT | 1,248,866 | 3.68 |
| 4 | TAGCTG | 1,251,788 | 3.69 |
| 5 | CACGTC | 1,293,928 | 3.82 |
| 6 | CATCGC | 1,324,504 | 3.91 |
| 7 | TGTCAC | 1,329,386 | 3.92 |
| 8 | GCCATG | 1,355,466 | 4.00 |
| 9 | CTGTGT | 1,374,184 | 4.05 |
| 10 | AGATCT | 1,385,126 | 4.08 |
| 11 | CTCACA | 1,393,690 | 4.11 |
| 12 | ATATGA | 1,407,292 | 4.15 |
| 13 | TGACAT | 1,414,096 | 4.17 |
| 14 | AGAGCT | 1,437,632 | 4.24 |
| 15 | TACACA | 1,439,688 | 4.25 |
| 16 | GTCAGT | 1,441,258 | 4.25 |
| 17 | CTAGAC | 1,448,142 | 4.27 |
| 18 | GTGATA | 1,459,940 | 4.31 |
| 19 | CAGCAC | 1,490,628 | 4.40 |
| 20 | ACGTCA | 1,495,158 | 4.41 |
| 21 | TGATAG | 1,511,516 | 4.46 |
| 22 | GCTGTG | 1,516,192 | 4.47 |
| 23 | ACTGCG | 1,828,876 | 5.39 |
| 24 | ACTGTA | 1,845,634 | 5.44 |
| Total number of reads | | 33,909,794 | 100% |

In the second experiment, the efficiency of sample normalisation was re-examined for pre-capture PCR. A pool of 24 sample libraries for next-generation sequencing was prepared by amplifying 500 ng of the non-biotinylated 300-bp DNA fragment used in the previous experiment for seven cycles of pre-capture PCR. Each pre-capture PCR was performed using biotinylated PE1 primer and a different indexed PE2 primer for each sample. The biotinylated pre-capture PCR products for the 24 samples were each incubated with MyOne™ beads providing a theoretical binding capacity of 62.5 ng of biotinylated DNA. After washing to remove unbound DNA, the MyOne™ beads were pooled and the immobilised fragments were released by heat elution. The released DNA was post-capture PCR amplified, quantified by qPCR and loaded in a single HiSeq2000 lane as a 5% spike (by volume). The percentage of indexed reads generated for each samples was used to assess the uniformity of sample capture to MyOne™ beads.

The percentage of sequence reads attributed to each of the 24 samples is shown in FIG. 5b. The average coverage across samples was 4.20±0.14%, which also approached the theoretical expectation (Table 7). 92% (22/24) of samples had a read coverage within a factor of 1.2 of the median and the CV was 0.12. These results were consistent with the qPCR analyses performed in the pilot experiments and confirm that seven cycles of pre-capture PCR generates sufficient biotinylated product to saturate the binding capacity of MyOne™ beads for efficient sample normalisation.

TABLE 7

Sample representation in 24-plex BeadPlex library.

| Sample | PE2 index | Number of reads | % Reads |
|---|---|---|---|
| 1 | GCGAGC | 1,125,598 | 3.32 |
| 2 | CACGTC | 1,257,166 | 3.71 |
| 3 | GATCAG | 1,273,588 | 3.76 |
| 4 | CATCGC | 1,303,294 | 3.84 |
| 5 | TGTCAC | 1,320,964 | 3.90 |
| 6 | GTCAGT | 1,330,194 | 3.92 |
| 7 | CTGTGT | 1,330,286 | 3.92 |
| 8 | CAGCAC | 1,343,808 | 3.96 |
| 9 | GCCATG | 1,348,750 | 3.98 |
| 10 | TGACAT | 1,368,194 | 4.03 |
| 11 | GTGATA | 1,417,700 | 4.18 |
| 12 | TGCTGT | 1,421,598 | 4.19 |
| 13 | AGATCT | 1,423,848 | 4.20 |
| 14 | GCTGTG | 1,433,742 | 4.23 |
| 15 | CTCACA | 1,444,606 | 4.26 |
| 16 | TACACA | 1,447,920 | 4.27 |
| 17 | ACGTCA | 1,456,084 | 4.29 |
| 18 | CTAGAC | 1,460,990 | 4.31 |
| 19 | TGATAG | 1,466,676 | 4.33 |
| 20 | TAGCTG | 1,467,872 | 4.33 |

TABLE 7-continued

Sample representation in 24-plex BeadPlex library.

| Sample | PE2 index | Number of reads | % Reads |
|---|---|---|---|
| 21 | AGAGCT | 1,485,586 | 4.38 |
| 22 | ATATGA | 1,487,542 | 4.39 |
| 23 | ACTGCG | 1,772,394 | 5.23 |
| 24 | ACTGTA | 1,992,474 | 5.88 |
| Total number of reads | | 34,180,874 | 100% |

The percentage of reads generated for each sample with the same barcode in the two experiments was similar (Pearson correlation coefficient, r=0.87), indicating that the variation observed was unlikely to be caused by bias during pre-capture PCR or sample immobilisation to MyOne™ beads. Hence, the small amount of unevenness in read coverage between samples was more likely caused during post-capture PCR by the index sequences used for sample tracking. PCR bias due to barcode sequences has been reported previously.

In the third experiment, the efficiency of sample normalisation was assessed for the entire BeadPlex protocol. Library pools with 12, 24 and 48 samples were prepared by fragmenting independent sources of DNA to an average size of 300-bp using a Covaris instrument, followed by end-repair and ligation of a non-biotinylated double-stranded DNA adapter. Four adapters with different internal barcodes were used for sample ligation. One µg of adapter-ligated DNA for each sample was amplified with seven cycles of pre-capture PCR to generate biotinylated product for sample normalisation. Pre-capture PCR was performed using biotinylated PE1 primer and a different indexed PE2 primer for each sample. The pre-capture PCR products were incubated with MyOne™ beads providing a theoretical binding capacity of 62.5 ng of biotinylated DNA. After washing to remove unbound DNA, the MyOne™ beads were pooled to make two 12-plex, one 24-plex and one 48-plex library. The immobilised DNA was released by heat elution, amplified by post-capture PCR, quantified by qPCR and loaded in three lanes on a HiSeq200 instrument as 5% spikes (by volume), with the two 12-plex libraries, 24-plex and 48-plex libraries loaded in the first, second and third lane, respectively. The percentage of indexed reads generated for each sample was used to assess the efficiency of BeadPlex sample normalisation.

The proportion of sequence reads attributed to each sample within the different BeadPlex libraries is shown in FIG. 6. Within the two 12-plex libraries, the average coverage across samples was 8.33±0.50 and 7.63±0.40%, which approached the theoretical expectation of 8.33% (Table 8). One sample within each 12-plex had a coverage greater than a factor of 1.5 of the median, and five and three samples had a coverage factor greater than 1.2 of the median, respectively. The CV for the two 12-plex was 0.21 and 0.18. For the 24-plex library, the average coverage across samples was 4.17±0.15%, which was very close to the theoretical expectation of 4.17% (Table 9). Two samples had a mean coverage greater than a factor of 1.5 of the median, and five samples had a factor greater than 1.2 of the median. The CV for the 24-plex was 0.17. For the 48-plex, the average coverage across samples was 2.08±0.01%, which was near the theoretical expectation of 2.08% (Table 10). Three (6%) samples had a read coverage greater than a factor of 2 of the median, nine (19%) samples had a read coverage greater than a factor of 1.5 of the median, and 30 (62%) samples had a factor greater than 1.2 of the median. The CV for the 48-plex was 0.32. Overall, the results for the 12-, 24- and 48-plex are consistent with the findings for the qPCR analyses performed in the pilot experiments and confirm that BeadPlex provides effective sample normalisation in library pools comprised of up to at least 48 samples. However, increased variation in sample representation was observed in the current BeadPlex libraries, compared to the two 12-plex libraries subjected to next-generation sequencing in the first and second experiments (compare FIGS. 5 and 6). The source of this variation requires further investigation as it is presently confounded by several factors including: 1) use of different sources of sample DNA between experiments, and 2) the use of adapters with internal indexing in the current (third) experiment. It is probable that the use of dual barcodes for sample indexing in this experiment is responsible for the observed increase in the unevenness for sample representation, since PCR bias for sample representation caused by barcode sequences is commonly reported.

TABLE 8

Sample representation in the two 12-plex BeadPlex library.

| Sample | PE2 index | Adapter index | Number of reads | % Reads | PE2 index | Adapter index | Number of reads | % Reads |
|---|---|---|---|---|---|---|---|---|
| 1 | TACACA | TGACT | 449,288 | 5.4 | GTGATA | GACTG | 403,100 | 4.8 |
| 2 | TAGCTG | GACTG | 483,317 | 5.8 | ACGTCA | GACTG | 504,417 | 6.1 |
| 3 | GATCAG | GACTG | 531,837 | 6.4 | CATCGC | GACTG | 565,156 | 6.8 |
| 4 | CAGCAC | CTGAC | 598,763 | 7.2 | GCGAGC | ACTGA | 582,154 | 7.0 |
| 5 | AGATCT | GACTG | 721,064 | 8.7 | ACTGTA | ACTGA | 611,029 | 7.3 |
| 6 | CTGTGT | ACTGA | 723,541 | 8.7 | CTCACA | CTGAC | 645,539 | 7.8 |
| 7 | GCCATG | CTGAC | 724,431 | 8.7 | CACGTC | TGACT | 645,862 | 7.8 |
| 8 | TGTCAC | CTGAC | 764,909 | 9.2 | TGACAT | CTGAC | 666,150 | 8.0 |
| 9 | AGAGCT | ACTGA | 789,273 | 9.5 | ACTGCG | TGACT | 699,156 | 8.4 |
| 10 | ATATGA | TGACT | 810,630 | 9.7 | GTCAGT | CTGAC | 708,813 | 8.5 |
| 11 | GCTGTG | ACTGA | 841,583 | 10.1 | TGATAG | TGACT | 737,785 | 8.9 |
| 12 | TGCTGT | TGACT | 888,377 | 10.7 | CTAGAC | ACTGA | 854,069 | 10.3 |
| Total number of reads | | | 8,327,013 | 100% | | | 7,623,230 | 100% |

TABLE 9

Sample representation in 24-plex BeadPlex library.

| Sample | PE2 index | Adapter Index | Number of reads | % Reads |
|---|---|---|---|---|
| 1 | TACACA | TGACT | 379,654 | 2.8 |
| 2 | TAGCTG | GACTG | 366,613 | 2.7 |
| 3 | GATCAG | GACTG | 458,141 | 3.4 |
| 4 | CAGCAC | CTGAC | 539,961 | 4.0 |
| 5 | AGATCT | GACTG | 536,357 | 4.0 |
| 6 | CTGTGT | ACTGA | 669,320 | 5.0 |
| 7 | GCCATG | CTGAC | 578,689 | 4.3 |
| 8 | TGTCAC | CTGAC | 623,619 | 4.6 |
| 9 | AGAGCT | ACTGA | 648,718 | 4.8 |
| 10 | ATATGA | TGACT | 708,773 | 5.2 |
| 11 | GCTGTG | ACTGA | 690,104 | 5.1 |
| 12 | TGCTGT | TGACT | 577,929 | 4.3 |
| 13 | GTGATA | GACTG | 406,761 | 3.0 |
| 14 | ACGTCA | GACTG | 488,716 | 3.6 |
| 15 | CATCGC | GACTG | 528,996 | 3.9 |

TABLE 9-continued

Sample representation in 24-plex BeadPlex library.

| Sample | PE2 index | Adapter Index | Number of reads | % Reads |
|---|---|---|---|---|
| 16 | GCGAGC | ACTGA | 491,501 | 3.6 |
| 17 | ACTGTA | ACTGA | 622,861 | 4.6 |
| 18 | CTCACA | CTGAC | 650,752 | 4.8 |
| 19 | CACGTC | TGACT | 516,406 | 3.8 |
| 20 | TGACAT | CTGAC | 530,905 | 3.9 |
| 21 | ACTGCG | TGACT | 578,943 | 4.3 |
| 22 | GTCAGT | CTGAC | 615,480 | 4.6 |
| 23 | TGATAG | TGACT | 617,773 | 4.6 |
| 24 | CTAGAC | ACTGA | 687,149 | 5.1 |
| Total number of reads | | | 13,514,121 | 100% |

TABLE 10

Sample representation in 48-plex BeadPlex library.

| Sample | PE2 index | Adapter Index | Number of reads | % Reads |
|---|---|---|---|---|
| 1 | GCGAGC | ACTGA | 68,904 | 0.77 |
| 2 | GATCAG | ACTGA | 73,402 | 0.82 |
| 3 | GCGAGC | CTGAC | 75,826 | 0.84 |
| 4 | CTAGAC | ACTGA | 94,711 | 1.05 |
| 5 | CAGCAC | CTGAC | 107,005 | 1.19 |
| 6 | GCTGTG | ACTGA | 107,804 | 1.20 |
| 7 | GATCAG | CTGAC | 124,707 | 1.39 |
| 8 | AGATCT | ACTGA | 125,776 | 1.40 |
| 9 | CACGTC | CTGAC | 126,007 | 1.40 |
| 10 | CAGCAC | ACTGA | 126,539 | 1.41 |
| 11 | AGATCT | CTGAC | 128,694 | 1.43 |
| 12 | GCGAGC | GACTG | 129,905 | 1.45 |
| 13 | TACACA | ACTGA | 148,258 | 1.65 |
| 14 | CACGTC | ACTGA | 153,041 | 1.70 |
| 15 | GCTGTG | CTGAC | 153,223 | 1.71 |
| 16 | GATCAG | TGACT | 156,097 | 1.74 |
| 17 | GCGAGC | TGACT | 157,725 | 1.76 |
| 18 | GTCAGT | CTGAC | 161,733 | 1.80 |
| 19 | TACACA | TGACT | 170,934 | 1.90 |
| 20 | GATCAG | GACTG | 172,453 | 1.92 |
| 21 | TACACA | CTGAC | 173,639 | 1.93 |
| 22 | TGACAT | CTGAC | 179,573 | 2.00 |
| 23 | CTGTGT | ACTGA | 183,968 | 2.05 |
| 24 | AGATCT | TGACT | 184,469 | 2.05 |
| 25 | CTAGAC | CTGAC | 190,636 | 2.12 |
| 26 | CAGCAC | TGACT | 203,086 | 2.26 |
| 27 | CTAGAC | GACTG | 204,351 | 2.28 |
| 28 | TGACAT | TGACT | 207,788 | 2.31 |
| 29 | GTCAGT | TGACT | 207,978 | 2.32 |
| 30 | AGATCT | GACTG | 211,365 | 2.35 |
| 31 | CACGTC | TGACT | 213,694 | 2.38 |
| 32 | TACACA | GACTG | 213,961 | 2.38 |
| 33 | CAGCAC | GACTG | 218,994 | 2.44 |
| 34 | GCTGTG | TGACT | 221,994 | 2.47 |
| 35 | CTGTGT | CTGAC | 228,423 | 2.54 |
| 36 | GCTGTG | GACTG | 238,649 | 2.66 |
| 37 | CTCACA | CTGAC | 242,167 | 2.70 |
| 38 | TGACAT | GACTG | 245,206 | 2.73 |
| 39 | CTCACA | GACTG | 247,322 | 2.75 |
| 40 | CTGTGT | GACTG | 249,826 | 2.78 |
| 41 | CACGTC | GACTG | 250,052 | 2.78 |
| 42 | GTCAGT | GACTG | 251,606 | 2.80 |
| 43 | CTGTGT | TGACT | 251,803 | 2.80 |
| 44 | CTCACA | TGACT | 255,265 | 2.84 |
| 45 | CTAGAC | TGACT | 255,884 | 2.85 |
| 46 | GTCAGT | ACTGA | 274,274 | 3.05 |
| 47 | CTCACA | ACTGA | 300,647 | 3.35 |
| 48 | TGACAT | ACTGA | 309,487 | 3.45 |
| Total number of reads | | | 8,978,851 | 100% |

Maintenance of Sample Representation

Maintenance of sample representation (or specificity) is of critical importance to any library preparation method for next generation sequencing. To determine if BeadPlex introduced any bias for sample representation, we compared the sequence outputs for 24 samples prepared using with and without Bearlex sample normalisation. The input DNA for each sample was derived from pooled PCR product (about 2,200 unique amplicons), generated by amplifying about a 1-kb region from the homoeologous copies of 732 genes from each of 24 hexaploid wheat varieties. Sample libraries were prepared by fragmenting the pooled PCR product to an average size of 300-bp using a Covaris instrument, followed by end-repair and ligation of a non-biotinylated double-stranded adapter. Four adapters with different internal barcodes were used for sample ligation. One μg of adapter-ligated DNA for each sample was amplified with seven cycles of pre-capture PCR using biotinylated PE1 primer and a different indexed PE2 primer for sample tracking. A 24-plex library was prepared without BeadPlex sample normalisation, and two 12-plex and one 24-plex library was prepared with BeadPlex sample normalisation. The BeadPlex libraries were prepared by incubating the pre-capture PCR products with MyOne™ beads providing a theoretical binding capacity of 62.5 ng of biotinylated DNA. The multiplexed libraries were sequenced as 5% spikes (by volume) on a HiSeq2000 instrument. Maintenance of sample representation was assessed by comparing the sequence coverage distribution for each sample prepared with and without BeadPlex sample normalisation. The sequence coverage distribution was calculated from the percentage of reads that could be mapped for each sample to contig sequences for the pooled amplicons used as input DNA.

Comparison of the sequence coverage distribution for each type of sample library showed that BeadPlex produced minimal (if any) bias for sample representation. The average Pearson correlation coefficient between the unnormalised and normalised samples was 0.901±0.010 and 0.884±0.010 in the two 12-plex libraries, and 0.889±0.007 in the 24-plex library (Table 11). Further analysis of the sequence coverage distribution showed that poor representation of some amplicons in the pooled PCR product used as input DNA for sample library preparation was mainly responsible for the observed differences in sequence coverage between the two library types. Amplicons with poor representation in the pooled PCR product had both low and variable sequence read coverage in both library types, which contributed to a reduced Pearson correlation coefficient (FIG. 7).

TABLE 11

Number of mapped sequence reads and Pearson correlation coefficients (r) for the sequence coverage distributions of 24 samples prepared with and without BeadPlex sample normalisation.

| | Unnormalised library | BeadPlex normalised libraries | | | | |
| | | 12-plex | | 12-plex | | 24-plex | |
| Sample | No. mapped reads | No. mapped reads | r | No. mapped reads | r | No. mapped reads | r |
|---|---|---|---|---|---|---|---|
| 1 | 1,470,269 | 470,956 | 0.865 | . | . | 430,987 | 0.864 |
| 2 | 1,375,759 | 421,970 | 0.919 | . | . | 368,814 | 0.917 |
| 3 | 1,398,848 | 713,982 | 0.947 | . | . | 469,180 | 0.937 |
| 4 | 1,158,522 | 646,797 | 0.926 | . | . | 573,358 | 0.919 |
| 5 | 1,368,198 | 568,779 | 0.912 | . | . | 459,002 | 0.907 |
| 6 | 1,310,525 | 609,786 | 0.901 | . | . | 504,830 | 0.894 |
| 7 | 1,406,911 | 666,842 | 0.850 | . | . | 554,248 | 0.847 |
| 8 | 1,165,584 | 347,380 | 0.953 | . | . | 297,463 | 0.943 |
| 9 | 1,623,230 | 623,004 | 0.845 | . | . | 516,485 | 0.846 |
| 10 | 1,441,072 | 382,669 | 0.884 | . | . | 294,453 | 0.876 |
| 11 | 1,629,831 | 572,173 | 0.898 | . | . | 432,174 | 0.890 |
| 12 | 1,282,320 | 568,056 | 0.915 | . | . | 535,312 | 0.908 |
| 13 | 1,332,668 | . | . | 579,418 | 0.942 | 486,370 | 0.940 |
| 14 | 1,319,361 | . | . | 523,166 | 0.872 | 421,940 | 0.869 |
| 15 | 1,399,719 | . | . | 461,678 | 0.914 | 390,406 | 0.911 |
| 16 | 1,480,151 | . | . | 536,985 | 0.861 | 430,649 | 0.857 |
| 17 | 1,348,155 | . | . | 490,459 | 0.884 | 502,023 | 0.884 |
| 18 | 1,191,303 | . | . | 551,663 | 0.927 | 456,472 | 0.923 |
| 19 | 1,226,875 | . | . | 514,981 | 0.899 | 520,860 | 0.898 |
| 20 | 1,516,124 | . | . | 451,445 | 0.834 | 426,464 | 0.838 |
| 21 | 1,230,493 | . | . | 326,256 | 0.818 | 333,582 | 0.822 |
| 22 | 1,394,145 | . | . | 714,895 | 0.866 | 576,383 | 0.863 |
| 23 | 1,210,512 | . | . | 408,426 | 0.895 | 399,525 | 0.897 |
| 24 | 1,437,195 | . | . | 572,436 | 0.900 | 498,165 | 0.895 |
| | | | 0.901 | | 0.884 | | 0.889 |

EXAMPLE 3

High-Throughput, Automatable Method for Highly Parallel Preparation of Samples for Next-Generation Sequencing Enables flexible and scalable preparation of samples for sequencing, and sequence output generated for each sample to be effectively managed.

For DNA capture-based GBS, it provides sample throughput and scalability required in the project and ensures a uniform sequence output for each sample.

BeadPlex was developed to enable efficient management of sequence output across sample number and data density.
  Up to 35 Gb (350 million PE reads) per HiSeq lane
  Within lane sample multiplexing
  Pooling samples into a single lane increases number of samples analysed per run
  A unique identifier tag (third read index) added to each sample library enables accurate downstream sample tracking
  Commercial kits currently support multiplexing of up to 96 samples FIG. 8 shows two rate limiting steps for processing large sample numbers.

BeadPlex may incorporate dual barcoding strategy for sample tracking.

Samples may be labelled with up to two unique identifier tags, providing maximum flexibility for multiplexing of large numbers of samples (see FIG. 9).

There is minimal effect of sample DNA fragment size on capture efficiency.

A series of experiments were performed to determine effect of sample DNA molecule size on repeatability of bead capture step (see Table 12).

TABLE 12

Effect of sample DNA molecule size on repeatability of bead capture step, based on five technical replicates.

| Sample DNA fragment size (bp) | CV# (%) |
|---|---|
| 125 | 6.59 |
| 325-375 | 6.81 |
| 375-425 | 4.59 |
| 425-525 | 3.77 |
| 525-575 | 5.77 |

CV = Coefficient of Variation.

There is a minimal effect of input amount of sample DNA on capture efficiency.

A series of experiments were performed to determine effect of variation in input amount of sample DNA on repeatability of bead capture step (see Table 13).

TABLE 13

Effect of input amount of sample DNA on capture efficiency, based on three technical replicates.

| Input amount of sample DNA (ng) | CV# (%) |
|---|---|
| 50 | 7.33 |
| 250 | 3.33 |
| 500 | 4.16 |
| 750 | 4.30 |
| 1000 | 6.58 |

CV = Coefficient of Variation.

There was a minimal effect of input amount of sample DNA on capture efficiency. Pre-capture PCR ensured sufficient (excess) product is generated for bead capture, even from as low as 50 ng input (see FIG. 10).

There was high repeatability between technical replicates.

A series of experiments was performed to determine overall technical repeatability of BeadPlex method. Based on 6 technical replicates the Coefficient of Variation was 10.3%.

There was a similar representation of samples in HiSeq sequence output (FIG. 11). The average CV for 12-plex libraries prepared using standard Illumina protocol is 15%.

SUMMARY

High throughput, automatable method for flexible and highly parallel preparation of samples for next-generation sequencing Provides significant time savings compared to current methods, especially as sample number increases Enables efficient partitioning of sequence output across data density and sample number Compatible with DNA and RNA Broad utility in molecular genetic and genomic research Finally, it is to be understood that various alterations, modifications and/or additions may be made without departing from the spirit of the present invention as outlined herein.

The invention claimed is:

1. A method of preparing a normalised nucleic acid library containing a plurality of nucleic acid species in pre-defined relative concentrations, said method including:
providing
a plurality of samples each containing a biotinylated nucleic acid species, and
a solid state capture material including streptavidin;
contacting each of the plurality of nucleic acid-containing samples with a limiting amount of the solid state capture material to provide capture some but not all of the nucleic acids from each of the nucleic-acid containing samples; and
pooling the captured nucleic acid samples, and optionally eluting the captured nucleic acids from the solid state capture material to provide the normalised nucleic acid library containing the plurality of nucleic acid species in relative concentrations determined by the amount of solid state capture material contacted with the sample;
wherein the nucleic acids are ligated to biotinylated adapter molecules and any unligated adapter molecules and incompetent nucleic acids with partially ligated adapter molecules are removed prior to capture by exonuclease III digestion;
wherein the library is a multiplexed library, and wherein the amount of each nucleic acid species in the library is substantially uniformly represented in the library; and
wherein said contacting step includes contacting an at least 2:1 excess of biotinylated nucleic acid with a limiting amount of solid state capture material.

2. The method according to claim 1, wherein the plurality of nucleic acid-containing samples are subjected to a pre-capture PCR amplification step.

3. The method according to claim 2, wherein the pre-capture PCR amplification step includes introducing barcodes via tailed oligonucleotide primers.

4. The method according to claim 1, wherein the solid state capture material includes streptavidin-coated beads.

5. The method according to claim 1, wherein the adapter molecules include PCR priming sites and the nucleic acids are subjected to a pre-capture PCR amplification step.

6. The method according to claim 1, wherein the nucleic acids are subject to PCR using specific tailed primers, one said tailed primers being biotinylated.

7. The method according to claim 1, wherein the captured nucleic acid samples are washed to substantially remove unbound nucleic acids from the samples or minimise their presence in the samples.

8. The method according to claim 1, wherein the pooled nucleic acids are eluted to generate the nucleic acid library.

9. The method according to claim 1, wherein said method is performed by a liquid handling robot.

10. A method of next generation sequencing or genotyping-by-sequencing, said method including
preparing a normalised nucleic acid library by the method according to claim 1, amplifying and/or titrating the nucleic acid library and
then performing next-generation sequencing or genotyping-by-sequencing.

11. A method according to claim 1, wherein said contacting step includes contacting between 2:1 and 16:1 excess of biotinylated nucleic acid with a fixed amount of solid state capture material.

* * * * *